(12) United States Patent
Coate et al.

(10) Patent No.: US 11,464,768 B2
(45) Date of Patent: Oct. 11, 2022

(54) PIMAVANSERIN ALONE OR IN COMBINATION FOR USE IN THE TREATMENT OF ALZHEIMER'S DISEASE PSYCHOSIS

(71) Applicant: ACADIA Pharmaceuticals Inc., San Diego, CA (US)

(72) Inventors: Bruce Duane Coate, San Diego, CA (US); James Randall Owen, Princeton, NJ (US); Mark Donald Knowles, San Diego, CA (US); Srdjan R. Stankovic, Flemington, NJ (US); James M. Youakim, Bryn Mawr, PA (US)

(73) Assignee: ACADIA Pharmaceuticals Inc., San Diego, CA (US)

( * ) Notice: Subject to any disclaimer, the term of this patent is extended or adjusted under 35 U.S.C. 154(b) by 136 days.

(21) Appl. No.: 16/471,543

(22) PCT Filed: Dec. 14, 2017

(86) PCT No.: PCT/US2017/066340
§ 371 (c)(1),
(2) Date: Jun. 19, 2019

(87) PCT Pub. No.: WO2018/118626
PCT Pub. Date: Jun. 28, 2018

(65) Prior Publication Data
US 2020/0237739 A1 Jul. 30, 2020

Related U.S. Application Data

(60) Provisional application No. 62/511,223, filed on May 25, 2017, provisional application No. 62/436,959, filed on Dec. 20, 2016.

(51) Int. Cl.
| | |
|---|---|
| *A61K 31/4468* | (2006.01) |
| *A61P 25/28* | (2006.01) |
| *A61P 25/18* | (2006.01) |
| *A61K 9/00* | (2006.01) |
| *A61K 31/13* | (2006.01) |
| *A61K 31/27* | (2006.01) |
| *A61K 31/445* | (2006.01) |
| *A61K 31/473* | (2006.01) |
| *A61K 31/549* | (2006.01) |
| *A61K 31/55* | (2006.01) |

(52) U.S. Cl.
CPC ........ *A61K 31/4468* (2013.01); *A61K 9/0053* (2013.01); *A61K 31/13* (2013.01); *A61K 31/27* (2013.01); *A61K 31/445* (2013.01); *A61K 31/473* (2013.01); *A61K 31/549* (2013.01); *A61K 31/55* (2013.01); *A61P 25/18* (2018.01); *A61P 25/28* (2018.01)

(58) Field of Classification Search
CPC .................................................. A61K 31/4468
See application file for complete search history.

(56) References Cited

U.S. PATENT DOCUMENTS

| | | |
|---|---|---|
| 3,983,234 A | 9/1976 | Sayers |
| 4,138,492 A | 2/1979 | Noverola et al. |
| 4,255,432 A | 3/1981 | Kluge et al. |
| 4,332,804 A | 6/1982 | Clark |
| 4,353,900 A | 10/1982 | Clark |
| 4,353,901 A | 10/1982 | Clark |
| 4,367,232 A | 1/1983 | Boix-Igleasias et al. |
| 4,853,394 A | 8/1989 | King |
| 5,025,013 A | 6/1991 | Barreau |
| 5,214,055 A | 5/1993 | Peglion et al. |
| 5,216,165 A | 6/1993 | Mobilio et al. |
| 5,461,066 A | 10/1995 | Gericke et al. |
| 5,595,872 A | 1/1997 | Wetterau, II et al. |
| 5,621,010 A | 4/1997 | Sueda |
| 5,707,798 A | 1/1998 | Brann |
| 5,795,894 A | 8/1998 | Shue |
| 5,837,730 A | 11/1998 | Javitt |

(Continued)

FOREIGN PATENT DOCUMENTS

| | | |
|---|---|---|
| CA | 984843 A | 3/1976 |
| CN | 104844502 A | 8/2015 |

(Continued)

OTHER PUBLICATIONS

Wood, Stacey, et al. "The Use of the Neuropsychiatric Inventory in Nursing Home Residents: Characterization and Measurement." Am. J. Geriatr. Psychiatr. (2000), vol. 8(1), pp. 75-83. (Year: 2000).*
Coiovic, Mirjana B., et al. "Acetylcholinesterase Inhibitors: Pharmacology and Toxicology." Current Neuropharmacology. (2013), vol. 11, pp. 315-335. (Year: 2013).*
Kennedy, Matthew E., et al. "The BACE1 inhibitor verubecestat (MK-8931) reduces CNS β-amyloid in animal models and in Alzheimer's disease patients." Sci. Transl. Med. (Nov. 2, 2016), vol. 8, pp. 1 of 13 through 13 of 13. (Year: 2016).*
Shigemon, Kenta, et al. "The factorial structure of the mini mental state examination (MMSE) in Japanese dementia patients." BMC Geriatrics. (2010), vol. 10, Issue 36, pp. 1 of 7 through 7 of 7. (Year: 2010).*

(Continued)

*Primary Examiner* — John S Kenyon
(74) *Attorney, Agent, or Firm* — Goodwin Procter LLP

(57) ABSTRACT

Methods for the treatment of Alzheimer's disease psychosis, or a symptom thereof, comprising administering pimavanserin. Also provided herein are methods for the treatment of delusions and/or hallucinations in a human with dementia comprising administering pimavanserin, or a pharmaceutically acceptable salt thereof. Also provided herein are methods for reducing NPI-NH score in a human with Alzheimer's Disease comprising administering pimavanserin, or a pharmaceutically acceptable salt thereof. Also provided herein are methods for reducing agitated behavior or aggressive behavior in a human with dementia comprising administering pimavanserin, or a pharmaceutically acceptable salt thereof.

16 Claims, 3 Drawing Sheets

(56) References Cited

U.S. PATENT DOCUMENTS

| | | |
|---|---|---|
| 5,869,488 A | 2/1999 | Shue |
| 5,877,173 A | 3/1999 | Olney et al. |
| 5,912,132 A | 6/1999 | Brann |
| 5,955,281 A | 9/1999 | Brann |
| 6,107,324 A | 8/2000 | Behan |
| 6,140,509 A | 10/2000 | Behan |
| 6,150,393 A | 11/2000 | Behan |
| 6,358,698 B1 | 3/2002 | Weiner et al. |
| 6,451,343 B1 | 9/2002 | Glinecke et al. |
| 6,479,480 B1 | 11/2002 | Moyes |
| 6,486,153 B1 | 11/2002 | Castro Pineiro |
| 6,670,137 B2 | 12/2003 | VanMechelen et al. |
| 6,756,393 B2 | 6/2004 | Andersson et al. |
| 6,815,458 B2 | 11/2004 | Andersson et al. |
| 6,911,452 B2 | 6/2005 | Schlienger |
| 7,022,698 B2 | 4/2006 | Hamied et al. |
| 7,041,667 B1 | 5/2006 | Armour et al. |
| 7,087,593 B2 | 8/2006 | Kelly et al. |
| 7,115,634 B2 | 10/2006 | Thurieau et al. |
| 7,217,719 B2 | 5/2007 | Schlienger |
| 7,253,186 B2 | 8/2007 | Andersson et al. |
| 7,351,707 B2 | 4/2008 | Schlienger |
| 7,393,861 B2 | 7/2008 | Thurieau et al. |
| 7,476,682 B2 | 1/2009 | Andersson et al. |
| 7,538,222 B2 | 5/2009 | Andersson et al. |
| 7,601,740 B2 | 10/2009 | Andersson et al. |
| 7,659,285 B2 | 2/2010 | Weiner et al. |
| 7,713,995 B2 | 5/2010 | Weiner et al. |
| 7,732,462 B2 | 6/2010 | Weiner et al. |
| 7,732,615 B2 | 6/2010 | Thygesen et al. |
| 7,790,899 B2 | 9/2010 | Tolf et al. |
| 7,816,383 B1 | 10/2010 | Bradford et al. |
| 7,820,695 B2 | 10/2010 | Weiner et al. |
| 7,858,789 B2 | 12/2010 | Thurieau et al. |
| 7,863,296 B2 | 1/2011 | Weiner et al. |
| 7,868,176 B2 | 1/2011 | Thygesen et al. |
| 7,875,632 B2 | 1/2011 | Weiner et al. |
| 7,923,564 B2 | 4/2011 | Thygesen et al. |
| 7,994,193 B2 | 8/2011 | Weiner et al. |
| 8,008,323 B2 | 8/2011 | Weiner et al. |
| 8,110,574 B2 | 2/2012 | Thurieau et al. |
| 8,227,487 B2 | 7/2012 | Weiner et al. |
| 8,236,960 B2 | 8/2012 | Thygesen et al. |
| 8,377,959 B2 | 2/2013 | Weiner et al. |
| 8,618,130 B2 | 12/2013 | Weiner et al. |
| 8,921,393 B2 | 12/2014 | Weiner et al. |
| 9,050,343 B2 | 6/2015 | Peters et al. |
| 9,211,289 B2 | 12/2015 | Weiner et al. |
| 9,296,694 B2 | 3/2016 | Andersson et al. |
| 9,446,037 B2 | 9/2016 | Mills et al. |
| 9,486,453 B2 | 11/2016 | Javitt |
| 9,566,271 B2 | 2/2017 | Weiner et al. |
| 9,757,366 B2 | 9/2017 | Mills et al. |
| 9,765,053 B2 | 9/2017 | Andersson et al. |
| 10,028,944 B2 | 7/2018 | Weiner et al. |
| 10,449,185 B2 | 10/2019 | Tejwani et al. |
| 10,517,860 B2 | 12/2019 | Parkinson |
| 10,525,046 B2 | 1/2020 | Weiner et al. |
| 10,597,363 B2 | 3/2020 | Carlos et al. |
| 10,646,480 B2 | 5/2020 | Tejwani et al. |
| 10,849,891 B2 | 12/2020 | Tejwani et al. |
| 10,953,000 B2 | 3/2021 | Parkinson |
| 10,981,870 B2 | 4/2021 | Carlos et al. |
| 10,981,871 B2 | 4/2021 | Carlos et al. |
| 11,135,211 B2 | 10/2021 | Burstein |
| 11,191,757 B2 | 12/2021 | Parkinson |
| 2002/0156068 A1 | 10/2002 | Behan |
| 2002/0165225 A1 | 11/2002 | Kankan et al. |
| 2004/0006081 A1 | 1/2004 | Burrows |
| 2004/0106600 A1 | 6/2004 | Andersson et al. |
| 2004/0213816 A1 | 10/2004 | Weiner et al. |
| 2004/0229908 A1 | 11/2004 | Nelson |
| 2005/0014757 A1 | 1/2005 | Andersson et al. |
| 2005/0148018 A1 | 7/2005 | Weiner et al. |
| 2005/0244862 A1 | 11/2005 | Brann |
| 2005/0256108 A1 | 11/2005 | Schlienger |
| 2005/0261278 A1 | 11/2005 | Weiner et al. |
| 2005/0261340 A1 | 11/2005 | Weiner et al. |
| 2005/0288328 A1 | 12/2005 | Weiner et al. |
| 2006/0094758 A1 | 5/2006 | Andersson et al. |
| 2006/0106063 A1 | 5/2006 | Thhygesen et al. |
| 2006/0111399 A1 | 5/2006 | Thhygesen et al. |
| 2006/0194778 A1 | 8/2006 | Andersson et al. |
| 2006/0194834 A1 | 8/2006 | Andersson et al. |
| 2006/0199794 A1 | 9/2006 | Schlienger |
| 2006/0199818 A1 | 9/2006 | Andersson et al. |
| 2006/0199842 A1 | 9/2006 | Weiner et al. |
| 2006/0204486 A1 | 9/2006 | Pyke et al. |
| 2006/0205710 A1 | 9/2006 | Schlienger |
| 2006/0205722 A1 | 9/2006 | Andersson et al. |
| 2006/0205780 A1 | 9/2006 | Thygesen et al. |
| 2006/0205781 A1 | 9/2006 | Thygesen et al. |
| 2006/0264465 A1 | 11/2006 | Weiner et al. |
| 2006/0264466 A1 | 11/2006 | Weiner et al. |
| 2006/0286610 A1 | 12/2006 | Brann |
| 2006/0292606 A1 | 12/2006 | Brann |
| 2007/0260064 A1 | 11/2007 | Tolf et al. |
| 2007/0264330 A1 | 11/2007 | Ragnar-Tolf |
| 2008/0051429 A1 | 2/2008 | van Kammen et al. |
| 2008/0280886 A1 | 11/2008 | Gant et al. |
| 2009/0053329 A1 | 2/2009 | Peters et al. |
| 2009/0082342 A1 | 3/2009 | Uldam et al. |
| 2009/0082388 A1 | 3/2009 | Hacksell |
| 2009/0186921 A1 | 7/2009 | Andersson et al. |
| 2014/0018348 A1 | 1/2014 | Javitt |
| 2014/0162942 A1 | 6/2014 | Ghosal et al. |
| 2014/0221395 A1 | 8/2014 | Dhanoa |
| 2014/0329903 A1 | 11/2014 | Burstein et al. |
| 2014/0349976 A1 | 11/2014 | Hacksell et al. |
| 2015/0231126 A1 | 8/2015 | Peters |
| 2015/0313888 A1 | 11/2015 | Mills et al. |
| 2016/0237036 A1 | 8/2016 | Andersson et al. |
| 2018/0037549 A1 | 2/2018 | Biljan |
| 2019/0030015 A1 | 1/2019 | Weiner et al. |
| 2019/0047955 A1 | 2/2019 | Carlos et al. |
| 2019/0117636 A1 | 4/2019 | Burstein |
| 2019/0216791 A1 | 7/2019 | Tejwani et al. |
| 2019/0231767 A1 | 8/2019 | Parkinson |
| 2019/0240211 A1 | 8/2019 | Parkinson |
| 2020/0009122 A1 | 1/2020 | Tejwani et al. |
| 2020/0061045 A1 | 2/2020 | Burstein |
| 2020/0078346 A1 | 3/2020 | Parkinson |
| 2020/0165202 A1 | 5/2020 | Carlos et al. |
| 2020/0181087 A1 | 6/2020 | Carlos et al. |
| 2020/0222381 A1 | 7/2020 | Tejwani et al. |
| 2020/0323836 A1 | 10/2020 | Weiner et al. |
| 2021/0077479 A1 | 3/2021 | Tejwani et al. |
| 2021/0161880 A1 | 6/2021 | Foff |
| 2021/0283118 A1 | 9/2021 | Tejwani et al. |
| 2022/0000852 A1 | 1/2022 | Burstein |

FOREIGN PATENT DOCUMENTS

| | | |
|---|---|---|
| CN | 104961672 A | 10/2015 |
| CN | 105111135 A | 12/2015 |
| CN | 105153016 A | 12/2015 |
| CN | 105418460 A | 3/2016 |
| CN | 105481757 A | 4/2016 |
| CN | 105820110 A | 8/2016 |
| CN | 106543072 A | 3/2017 |
| EP | 0005318 B1 | 11/1979 |
| EP | 0061333 B1 | 9/1982 |
| EP | 0260070 B1 | 3/1988 |
| EP | 0379441 A1 | 7/1990 |
| EP | 0548015 B1 | 6/1993 |
| EP | 0625507 B1 | 11/1994 |
| EP | 1576985 A1 | 9/2005 |
| HU | 157325 | 3/1998 |
| JP | 51052176 | 5/1976 |
| JP | 52085174 A | 7/1977 |
| WO | WO-9427967 A1 | 12/1994 |
| WO | WO-9708166 A1 | 3/1997 |
| WO | WO-9711940 A1 | 4/1997 |
| WO | WO-9738665 A2 | 10/1997 |

(56) References Cited

FOREIGN PATENT DOCUMENTS

| | | |
|---|---|---|
| WO | WO-9738984 A1 | 10/1997 |
| WO | WO-9811128 A1 | 3/1998 |
| WO | WO-9817646 A1 | 4/1998 |
| WO | WO-98/44921 A1 | 10/1998 |
| WO | WO-98/50534 A1 | 11/1998 |
| WO | WO-9952927 A1 | 10/1999 |
| WO | WO-0023076 A1 | 4/2000 |
| WO | WO-0056335 A1 | 9/2000 |
| WO | WO-0059497 A1 | 10/2000 |
| WO | WO-0069810 A1 | 11/2000 |
| WO | WO-0144191 A1 | 6/2001 |
| WO | WO-0166521 A1 | 9/2001 |
| WO | WO-0187839 A1 | 11/2001 |
| WO | WO-2001089498 A2 | 11/2001 |
| WO | WO-0224649 A1 | 3/2002 |
| WO | WO-2002038142 A2 | 5/2002 |
| WO | WO-02076464 A1 | 10/2002 |
| WO | WO-02079186 A2 | 10/2002 |
| WO | WO-03057698 A2 | 7/2003 |
| WO | WO-03062206 A2 | 7/2003 |
| WO | WO-03070246 A1 | 8/2003 |
| WO | WO-03086400 A1 | 10/2003 |
| WO | WO-04000808 A2 | 12/2003 |
| WO | WO-04039322 A2 | 5/2004 |
| WO | WO-04064753 A2 | 8/2004 |
| WO | WO-2004064738 A2 * | 8/2004 ............... A61K 9/20 |
| WO | WO-05053796 A1 | 6/2005 |
| WO | WO-05063254 A2 | 7/2005 |
| WO | WO-05112927 A1 | 12/2005 |
| WO | WO-06036874 A1 | 4/2006 |
| WO | WO-2006037043 A1 | 4/2006 |
| WO | WO-06104826 A2 | 10/2006 |
| WO | WO-2007124136 A1 | 11/2007 |
| WO | WO-2007133802 A2 | 11/2007 |
| WO | WO-2008116024 A2 | 9/2008 |
| WO | WO-2008141057 A1 | 11/2008 |
| WO | WO-2008144326 A2 | 11/2008 |
| WO | WO-2008144665 A1 | 11/2008 |
| WO | WO-2009035473 A2 | 3/2009 |
| WO | WO-2009039460 A2 | 3/2009 |
| WO | WO-2009039461 A2 | 3/2009 |
| WO | WO-2010111353 A1 | 9/2010 |
| WO | WO-2011047341 A2 | 4/2011 |
| WO | WO-2011085216 A2 | 7/2011 |
| WO | WO-2014085362 A1 | 6/2014 |
| WO | WO-2016201373 A1 | 12/2016 |
| WO | WO-2017011767 A2 | 1/2017 |
| WO | WO-2017015272 A1 | 1/2017 |
| WO | WO-2017165635 A1 | 9/2017 |
| WO | WO-2017172757 A1 | 10/2017 |
| WO | WO-2018118626 A1 | 6/2018 |
| WO | WO-2018200977 A1 | 11/2018 |
| WO | WO-2019046167 A1 | 3/2019 |
| WO | WO-2019177973 A1 | 9/2019 |
| WO | WO-2020092618 A1 | 5/2020 |
| WO | WO-2021016369 A1 | 1/2021 |
| WO | WO-2021030607 A1 | 2/2021 |

OTHER PUBLICATIONS

Hacksell, Uli., et al. "On the Discovery and Development of Pimavanserin: A Novel Drug Candidate for Parkinson's Psychosis." Neurochem. Res. (2014), vol. 39, pp. 2008-2017. (Year: 2014).*

"ACP-103," *Drugs of the Future, Prous Science* (2006) vol. 31, No. 11, pp. 939-943.

"NUPLAZID™ (pimavanserin) Sponsor Background Information for a Meeting of the Psychopharmacologic Drugs Advisory Committee on Mar. 29, 2016," Acadia Pharmaceuticals Inc., 2016. Retrieved from the Internet (URL): <https://www.fda.gov/downloads/advisorycommittees/committeesmeetingmaterials/drugs/psychopharmacologicdrugsadvisorycommittee/ucm492453.pdf> (173 pages).

"Pimavanserin (Nuplazid) for parkinson's disease psychosis," Medical Letter on Drugs and Therapeutics, New Rochelle, NY, US (Jun. 2016) vol. 58, pp. 74-75.

Aarsland et al., "Decreased burden among caregivers of patients with Parkinson's disease psychosis (PDP) treated with pimavanserin, a selective 5-HT2A inverse agonist," (Meeting Abstract) *Neurology* (2015) vol. 84, No. 14, Suppl P6.044.

Abbas et al., "Pimavanserin tartrate: a 5-HT2A inverse agonist with potential for treating various neuropsychiatric disorders," *Expert Opinion on Pharmacotherapy* (2008) vol. 9, No. 18, pp. 3251-3259.

Adam, et al., "Effects of repeated ritanserin on middle-aged poor sleepers," *Psychopharmacology* (1989) 99:219-221.

Aizenstein et al., "Frequent Amyloid Deposition Without Significant Cognitive Impairment Among the Elderly," Arch. Neurol. 65(11):1509-1517 (2008).

Akin, et al., "Decreased serotonin 5-HT 2A receptor-stimulated phosphoinositide signaling in fibroblasts from melancholic depressed patients," *Neuropsychopharmacology* (2004) 29:2081-2087.

Al Bujuq, N. R. "Methods of synthesis of Pimavanserin: the first drug approved for the treatment of Parkinson's disease psychosis (PDP)." Arkivoc. 2020. pp. 340-352.

Antunes, et al., "The novel object recognition memory: neurobiology, test procedure, and its modifications," *Cogn. Process* (2012) 13:93-110.

Bakshi, et al., "Clozapine antagonizes phencyclidine-induced deficits in sensorimotor gating of the startle response," *The Journal of Pharmacology and Experimental Therapeutics* (1994) 271(2):787-794.

Basha, A., "Synthesis of N, N'-disubstituted Ureas from Carbamates," Tetrahedron Letters 29(21):2525-2526 (1988).

Bennett, et al., "Suppression of dyskinesias in advanced Parkinson's disease. II. Increasing daily clozapine doses suppress dyskinesias and improve parkinsonism symptoms," *Neurology* (1993) 43:1551-1554.

Bhana et al., "A Review of its Use in the Management of the Behavioral and Psychological Symptoms of Dementia," Drugs & Aging 16(6):451-471 (2000).

Biagi, et al., "1,2,3-Triazoles: Structural changes on two effective inhibitors of the prostaglandin synthesis in vitro," *Farmaco Ed. Sci.* (1988) 43:597-611.

Bibbiani, et al., "Serotonin 5-HT1A agonist improves motor complications in rodent and primate parkinsonian models," *Neurology* (2001) 57:1829-1834.

Blakley, et al., "Bidirectional changes in ethanol consumption in rats with site-specific antisense down-regulation of 5-hydroxytryptamine2A receptors in brain," *The Journal of Pharmacology and Experimental Therapeutics* (2001) 299(1):277-289.

Blier, et al., "Potential mechanisms of action of atypical antipsychotic medications in treatment-resistant depression and anxiety," *J. Clin. Psychiatry* (2005) 66(suppl 8):30-40.

Blier, et al., "Putative mechanisms of action of antidepressant drugs in affective and anxiety disorders and pain," *Journal of Psychiatry & Neuroscience* (2001) 26(1):37-43.

Bogolubsky et al., "Bis(2,2,2-trifluoroethyl) carbonate as a condensing agent in one-pot parallel synthesis of unsymmetrical aliphatic ureas," (2014), pp. S1-S67. Retrieved from URL: http://pubs.acs.org/doi/suppl/I 0.102 I/co500025f/supl_file co500025f_si_001.pdf, Table S2, pp. S9, entry 47.

Bogolubsky et al., "Bis(2,2,2-trifluoroethyl) carbonate as a condensing agent in one-pot parallel synthesis of unsymmetrical aliphatic ureas," *ACS Combinatorial Science* (2014) vol. 16, Issue 6, pp. 303-308.

Bond et al., "Physiological effects of inverse agonists in transgenic mice with myocardial overexpression of the beta-adrenoceptor," *Nature* (1995) 374:272-276.

Borman et al., "5-HT2B receptors play a key role in mediating the excitatory effects of 5-HT in human colon in vitro," *Br. J. Pharmacol.* (2002) vol. 135, No. 5, pp. 1144-1151.

Brann, M. R. "Identification of ligands by selective amplification of cells transfected with receptors and marker enzymes," *Chemical Abstracts* (1998) 128: 111548.

Chaturvedi, D., "Perspectives on the Synthesis of Organic Carbamates," Tetrahedron 68:15-45 (2012).

(56) References Cited

OTHER PUBLICATIONS

Chaturvedi, D., "Recent Developments on the Carbamation of Amines," Curr. Org. Chem. 15:1593-1624 (2011).
Choi et al., "5HT2B receptor-mediated serotonin morphogenic functions in mouse cranial neural crest and myocardial cells," *Development* (1997) vol. 124, pp. 1745-1755.
Cirrito et al., "Serotonin signaling is associated with lower amyloid-p levels and plaques in transgenic mice and humans," *PNAS* (2011) vol. 108, No. 36, pp. 14968-14973.
Cummings et al., "Pimavanserin for patients with Parkinson's disease psychosis: a randomised, placebo-controlled phase 3 trial," *Lancet* (2014) vol. 383, pp. 533-540.
Cummings et al., "Pimavanserin: Potential Treatment for Dementia-Related Psychosis." J. Prev. Alzheimer's Dis. 5(4): 253-258 (2018).
Database CA [online] Chemical Abstracts Service, Columbus, Ohio, US; 2016, WANG et al., "Intermediate of pimavanserin and its analog, preparation method thereof and preparation method of pimavanserin and its analog," XP002761533, retrieved from STN Database accession No. 2016:451070 (reference date: Mar. 23, 2016).
Database CA [online] Chemical Abstracts Service, Columbus, Ohio, US; 2016, Zheng, Xuchun et al: "A process for preparing pimavanserin tartrate," XP002761538, retrieved from STN Database accession No. 2016:1261850 (reference date: Aug. 3, 2016).
Database WPI Week 201622, Derwent Publications Ltd., London, GB; AN 2016-17318M, XP002761536 (reference date: Aug. 19, 2015).
Database WPI Week 201623, Derwent Publications Ltd., London, GB; AN 2015-708058, XP002761532 (reference date: Oct. 7, 2015).
Database WPI Week 201635, Derwent Publications Ltd., London, GB; AN 2016-02257F, XP002761534 (reference date: Dec. 2, 2015).
Database WPI Week 201640, Derwent Publications Ltd., London, GB; AN 2016-01442V, XP002761535 (reference date: Dec. 16, 2015).
Database WPI Week 201641, Derwent Publications Ltd., London, GB; AN 2016-24419S, XP002761537 (reference date: Apr. 13, 2016).
DeClerck, et al., "Increase in slow-wave sleep in humans with the serotonin-S2 antagonist ritanserin," *Current Therapeutic Research* (1987) 41(4):427-432.
Delecluse, et al., "A case of tardive tremor successfully treated with clozapine," *Movement Disorders* (1998) 13(5):846-847.
Dine et al., "One-Pot, Solvent-Free Access to Unsymmetrical Ureas by Palladium-Catalysed Reductive Alkylation Using Molecular Hydrogen," Eur. J. Chem., 5445-5454 (2013).
Dube et al., "Carbonyldiimidazole-Mediated Lossen Rearrangement." Org. Lett. 11 (24):5622-5625 (2009).
Dunn, et al., "Analgetic and antiinflammatory 7-aroylbenzofuran-5-ylacetic acids and 7-aroylbenzothiophene-5-ylacetic acids," *J. Med. Chem.* (1986) 29:2326-2329.
Durif, et al., "Low-dose clozapine improves dyskinesias in Parkinson's disease," *Neurology* (1997) 48:658-662.
Eichelbaum, et al., "Influence of pharmacogenetics on drug disposition and response," *Clinical and Experimental Pharmacology and Physiology* (1996) 23:983-985.
Everett, et al., "L-Dopa: Effect on concentrations of dopamine, norepinephrine, and serotonin in brains of mice," *Science* (1970) 168:849-850.
Factor, et al. "Clozapine for the treatment of drug-induced psychosis in Parkinson's disease: Results of the 12 week open label extension in the PSYCLOPS trial," *Movement Disorders* (2001) 16(1):135-139.
Factor, et al., "Clozapine prevents recurrence of psychosis in Parkinson's disease," *Movement Disorders* (1992) 7(2):125-131.
Fava, M. et al. "A Phase 2, Randomized, Double-Blind, Placebo-Controlled Study of Adjunctive Pimavanserin in Patients with Major Depressive Disorder and an Inadequate Response to Therapy (CLARITY)." J Clin Psychiatry. Sep. 24, 2019;80(6) (13 pages).

Fitzgerald et al., "Possible Role of Valvular Serotonin 5-HT2B Receptors in the Cardiopathy Associated with Fenfluramine," *Molecular Pharmacol*. (1999) vol. 57, pp. 75-81.
Friedman et al., "A Multi-Center, Placebo-Controlled, Double-Blind Trial to Examine the Safety and Efficacy of Pimavanserin in the Treatment of Psychosis in Parkinson's Disease," *Neurology* (2010) vol. 74, No. 9, Suppl. 2, pp. A299.
Friedman, et al., "Atypical antipsychotics in the treatment of drug-induced psychosis in Parkinson's disease," *Movement Disorders* (2000) 15(2):201-211.
Friedman, et al., "Low-dose clozapine for the treatment of drug-induced psychosis in Parkinson's disease," N. Engl. J. Med. (1999) 340(10):757-763.
Friedman, J. H. "Clozapine treatment of psychosis in patients with tardive dystonia: Report of three cases," *Movement Disorders* (1994) 9(3):321-324.
Gillman, P. K. "Monoamine oxidase inhibitors, opioid analgesics and serotonin toxicity," *British Journal of Anaesthesia* (2005) 95(4):434-441.
Goldman et al., "Genetic counseling and testing for Alzheimer disease: Joint practice guidelines of the American College of Medical Genetics and the National Society of Genetic Counselors," *Genetics in Medicine* (2011) vol. 13, No. 6, pp. 597-605.
Hacksell et al., 2014, "On the Discovery and Development of Pimavanserin: A Novel Drug Candidate for Parkinson's Psychosis," Neurochem. Res., vol. 39, pp. 2008-2017.
Han et al., "Synthesis of Carbamates and Ureas Using Zr(IV)-Catalyzed Exchange Processes," Organic Letters 9(8): 1517-1520 (2007).
Hatoum, H. T. et al., "The Use of the Occupational Disruptiveness Scale of the Neuropsychiatric Inventory-Nursing Home Version to Measure the Impact of Rivastigmine on the Disruptive Behavior of Nursing Home Residents with Alzheimer's Disease," *Journal of the American Medical Directors Association* (2005) vol. 6, No. 4, pp. 238-245.
Highlights of Prescribing Information NUPLAZID™ (pimavanserin), Revised Apr. 2016. Retrieved from the Internet (URL): https://www.accessdata.fda.gov/drugsatfda_docs/label/2016/207318lbl.pdf (14 pages).
Highlights of Prescribing Information NUPLAZID® (pimavanserin), Revised Jun. 2018. Retrieved from the Internet (URL): https://www.accessdata.fda.gov/drugsatfda_docs/label/2018/207318s005lbl.pdf(15 pages).
Highlights of Prescribing Information NUPLAZID® (pimavanserin), Revised Mar. 2018. Retrieved from the Internet (URL): https://www.accessdata.fda.gov/drugsatfda_docs/label/2018/207318s002s004lbl.pdf (15 pages).
Idzikowski, et al. 1991. A dose response study examining the effects of ritanserin on human slow wave sleep. Br. J. Clin. Pharmac., 31:193-196.Idzikowski, et al., "A dose response study examining the effects of ritanserin on human slow wave sleep," *Br. J. Clin. Pharmac.* (1991) 31:193-196.
International Search Report and Written Opinion for International Application No. PCT/US2013/071792, dated Jan. 1, 2014 (9 pages).
International Search Report and Written Opinion in corresponding PCT Application PCT/US2016/042933 dated Oct. 14, 2016 (13 pages).
International Search Report and Written Opinion in corresponding PCT Patent Application No. PCT/US08/057557 dated Oct. 24, 2008 (10 pages).
International Search Report and Written Opinion in corresponding PCT Patent Application No. PCT/US2017/023795 dated May 29, 2017 (11 pages).
International Search Report and Written Opinion in corresponding PCT Patent Application No. PCT/US2017/024526 dated Jul. 5, 2017 (18 pages).
International Search Report and Written Opinion in corresponding PCT Patent Application No. PCT/US2017/066340 dated Mar. 5, 2018 (13 pages).
International Search Report and Written Opinion in corresponding PCT Patent Application No. PCT/US2018/029831 dated Jul. 11, 2018 (10 pages).

(56) References Cited

OTHER PUBLICATIONS

International Search Report and Written Opinion in corresponding PCT Patent Application No. PCT/US2018/048096 dated Oct. 30, 2018 (12 pages).
International Search Report and Written Opinion of the International Searching Authority for International Application No. PCT/US2019/021618 dated Jun. 12, 2019 (10 pages).
International Search Report and Written Opinion of the International Searching Authority for International Application No. PCT/US2019/058927 dated Jan. 23, 2020 (16 pages).
Ito et al., "Prediction of Human Drug Clearance from in Vitro and Preclinical Data Using Physiologically Based and Empirical Approaches," Pharm. Res., (2005) vol. 22, No. 1, pp. 103-112.
Kalgutkar, et al., "Selective inhibitors of monoamine oxidase (MAO-A and MAO-B) as probes of its catalytic site and mechanism," *Medicinal Research Reviews* (1995) 15(4)325-388.
Katritzky et al., Chapter V. "Reaction of Amines with Carbamic Acid Esters," Comprehensive Organic Functional Group Transformations, pp. 501-502 (1995).
Kondo et al., "Novel Ruthenium-Complex Catalyzed Synthesis of Ureas from Formamides and Amines," Organometallics 16:2562-2570 (1997).
Kotachi et al., "Ruthenium catalysed N.N'-Diarylurea Synthesis from N-Aryl Substituted Formamides and Aminoarenes," J. Chem. Soc., Chem. Comm., 7:549-550 (1990).
Lane et al., "Alzheimer's Disease," Eur. J. Neurol. 25:59-70 (2018).
Leysen, et al. "Serotonergic component of neuroleptic receptors," *Nature* (1978) 272:168-171.
Liechti, et al., "Effects of MDMA (ecstasy) on prepulse inhibition and habituation of startle in humans after pretreatment with Citalopram, Haloperidol, or Ketanserin," *Neuropsychopharmacology* (2001) 24(3):240-252.
Linder, et al. "Pharmacogenetics: A laboratory tool for optimizing therapeutic efficiency," *Clinical Chemistry* (1997) 43(2):254-266.
Loudon et al., "Conversion of Aliphatic Amides into Amines with [I,I-Bis(trifluoroacetoxy)iodo]benzene. 1. Scope of Reaction," J. Org. Chem. 49:4272-4276 (1984).
Marek et al., "The Selective 5-HT2A receptor Antagonist MI00907 Enhances Antidepressant-Like Behavioral Effects of the SSRI Fluoxetine," *Neuropsychopharmacology* (2005) vol. 30, No. 12, pp. 2205-2215.
Marek, et al., "Synergistic action of 5-HT2A antagonists and selective serotonin reuptake inhibitors in neuropsychiatric disorders," *Neuropsychopharmacology* (2003) 28:402-412.
Matsumura et al., "A New Method for Synthesis of Unsymmetrical Ureas Using Electrochemically Prepared Trifluoroethyl Carbamates," J. Org. Chem. 65:1549-1551 (2000).
Medical Review(s), Application No. 207318Orig1s000, Center for Drug Evaluation and Research, Submission Date Sep. 1, 2015 [available online Jun. 3, 2016]. Retrieved from the Internet (URL): <https://www.accessdata.fda.gov/drugsatfda_docs/nda/2016/207318Orig1s000MedR.pdf> (173 pages).
Meltzer et al., "Co-therapy with pimavanserin and risperidone 2 mg provides an improved clinical profile," *Schizophrenia Research* (2008) vol. 98, pp. 16.
Meltzer et al., "Pimavanserin, a Serotonin(2A) Receptor Inverse Agonist, for the Treatment of Parkinson's Disease Psychosis," *Neuropsychopharmacology* (2010) vol. 35, No. 4, pp. 881-892.
Meltzer et al., "Serotonin Receptors: Their Key Role in Drugs to Treat Schizophrenia," *Progress in Neuro-Pyschopharmacology & Biol. Psych.* (2003) vol. 27, pp. 1159-1172.
Meltzer, et al., "Plasma clozapine levels and the treatment of L-DOPA-induced psychosis in Parkinson's disease," *Neuropsychopharmacology* (1995) 12(1):39-45.
Meltzer, H. Y. "The role of serotonin in antipsychotic drug action," *Neuropsychopharmacology* (1999) 21 (2S): 106S-115S.
Morley et al., "Antibody to Amyloid p Protein Alleviates Imparied Acquisition, Retention, and Memory Processing in SAMP8 Mice," *Neurobiology of Learning and Memory* (2002), 78(1):125-138.

Naritomi et al., "Prediction of human hepatic clearance from in vivo animal experiments and in vitro metabolic studies with liver microsomes from animals and humans," *Drug Metab. Dispos.* (2001) vol. 29, No. 10, pp. 1316-1324.
NDA Approval/Supplement Approval, NDA 210793 NDA 207318/S-003, Letter Signed Jun. 28, 2018. Retrieved from the Internet (URL): https://www.accessdata.fda.gov/drugsatfda_docs/appletter/2018/210793Orig1s000,207318Orig1s003ltr.pdf (5 pages).
Nebigil et al., "Serotonin is a novel survival factor of cardiomyocytes: mitochondria as a target of 5-HT2B-receptor signaling," *FASEB J.* (2003) vol. 27, No. 10, pp. 1373-1375.
Ng, et al., "L-dopa-induced release of cerebral monoamines," *Science* (1970) 170:76-77.
Nordstrom, et al., "High 5-HT2 receptor occupancy in clozapine treated patients demonstrated by PET," *Psychopharmacology* (1993) 110:365-367.
Norton et al., "Caregivers of PDP patients have an increased risk of developing emotional and social distress that is decreased when PDP is treated with pimavanserin," (Meeting Abstract) *Journal of Parkinson's Disease* (Sep. 2016) vol. 6, No. S1, pp. 257, Abstract No. P42.11.
Norton et al., "Decreased burden among caregivers of patients with Parkinson's disease psychosis (PDP) treated with pimavanserin, a selective 5-HT2A inverse agonist," (Meeting Abstract) *Journal of Parkinson's Disease* (Sep. 2016) vol. 6, No. S1, p. 88, Abstract No. P12.08.
Obach et al., "The Prediction of Human Pharmacokinetic Parameters from Preclinical and In Vitro Metabolism Data," *J. Pharm. Exp. Therap.* (1997) vol. 283, No. 1, pp. 46-58.
Ogawa, et al., "Effects of R-102444 and its active metabolite R-96544, selective 5-HT2A receptor antagonists, on experimental acute and chronic pancreatitis: Additional evidence for possible involvement of 5-HT2A receptors in the development of experimental pancreatitis," *European Journal of Pharmacology* (2005) 521:156-163.
Paiva, et al., "Effects of ritanserin on sleep disturbances of dysthymic patients," *Psychopharmacology* (1988) 96:395-399.
Patel, et al., "The highly selective 5-hydroxytryptamine (5-HT)2A receptor antagonist, EMO 281014, significantly increases swimming and decreases immobility in male congenital learned helpless rats in the forced swim test," *Synapse* (2004) 52:73-75.
Pierce, et al., "5-hydroxytryptamine-induced synovial plasma extravasation is mediated via 5-hydroxytryptamine2A receptors on sympathetic efferent terminals," *The Journal of Pharmacology and Experimental Therapeutics* (1995) 275(1):502-508.
Poewe, W. "Psychosis in Parkinson's disease," *Movement Disorders* (2006) vol. 18, Suppl. 6, pp. S80-S87.
Pollak, et al., "Clozapine in drug-induced psychosis in Parkinson's disease," *Lancet* (1999) 353:2041-2042.
Price et al., "Pimavanserin, a 5-HT2A receptor inverse agonist, reverses psychosis-like behaviors in a rodent model of Alzheimer's disease," *Behavioural Pharmacology* (2002), 23:426-433.
R&D Focus Drug News (Jan. 24, 2000). Pimvaserin ACADIA lead compounds identified.
R&D Focus Drug News (Nov. 12, 2001). Pimvaserin ACADIA preclinical data.
Sadzot, et al., "Hallucinogenic drug interactions at human brain 5-HT2 receptors: Implications for treating LSD-induced hallucinogenesis," *Psychopharmacology* (1989) 98:495-499.
Saltzman, et al., "Cloning of the human serotonin 5-HT2 and 5-HT1C receptor subtypes," *Biochemical and Biophysical Research Communications* (1991) 181(3):1469-1478.
Sandler and Karo, Chapter E., "Reaction of Amines with Urethanes and Carbamates," Organic Functional Group Preparations, Academic Press pp. 161-162 (1986).
Satori and Maggi, "Acyclic and Cyclic Ureas," Science of Synthesis 18: 695-699 (2005).
Saxena, et al., "Cardiovascular effects of serotonin agonists and antagonists," *Journal of Cardiovascular Pharmacology* (1990) 15(Supp. 7):S17-S34.
Shanmugam, S. "Granulation Techniques and Technologies: Recent Progresses," *BioImpacts* (2015) vol. 5, No. 1, pp. 55-63.

(56) References Cited

OTHER PUBLICATIONS

Stoner et al., "Integrated oral bioavailability projection using in vitro screening data as a selection tool in drug discovery," *Int. J. Pharm.* (2004) vol. 269, No. 1, pp. 241-249.
Swedish Search Report for Patent Application No. 1730232-4 dated Mar. 28, 2018 (10 pages).
Thavonekham, "A Practical Synthesis of Ureas from Phenyl Carbamates," Synthesis 11:1189-1194 (1997).
Vanover et al., "Pharmacological Characterization of AC-90179 [2-(4-Methoxy-phenyl)-N-(4-methyl-benzyl)-N-(1-methyl-piperidiny-4-yl)-acetamide Hydrochloride]: A Selective Serotonin 2A Receptor Inverse Agonist," *J. Pharmacology & Experimental Therapeutics* (2004) vol. 310, No. 3, pp. 943-951.
Vanover, Kimberly E. et al., "Pharmacokinetics, tolerability, and safety of ACP-103 following single or multiple oral dose administration in healthy volunteers," *Journal of Clinical Phamacol.* (2007) vol. 47, No. 6, pp. 704-714.
Vinogradova et al., Palladium Catalyzed Cross-Coupling of Aryl Chlorides and Tritiates with Sodium Cyanate: A Practical Synthesis of Unsymmetrical Ureas, J. Am. Chem. Soc. 134:11132-11135 (2012).
Volk et al., "Synthesis of methyl ethyl and phenyl 4 2 methylpropoxy benzyl carbamates," The IP.com Prior Art Database, Disclosure No. IPCOM000244271D, (Nov. 27, 2015).
Yoshimura et al., "Hypervalent Iodine Catalyzed Hofmann Rearrangement of Carboxamides Using Oxone as Terminal Oxidant," JOC 77:11399-11404 (2012).
Yoshimura et al., (Tosylimino)phenyl-λ3-iodane as a Reagent for the Synthesis of Metyl Carbamates via Hofmann Rearrangement of Aromatic and Aliphatic Carboxamides, Journal of Organic Chemistry 77:2087-2091 (2012).
Anonymous, "Use of Liquids and/or Soft Foods as Vehicles for Drug Administration: General Considerations for Selection and In Vitro Methods for Product Quality Assessments Guidance for Industry," Jul. 13, 2018 (Jul. 13, 2018), XP055676101, Retrieved from the Internet: URL:https://www.fda.gov/media/114872/downl <http://www.fda.gov/media/114872/downl> oad [retrieved on Mar. 12, 2020].
Bekris et al. "Cerebrospinal Fluid Ab42 Levels and APP processing pathway genes in Parkinson's disease," Movement Disorders, 2015, vol. 30, No. 7, pp. 936-944, 2015.
Buddhala et al. "Correlation between descreased CSF a-synuclein and Ab1-42 in Parkinson disease," Neurobiology of Aging, 2015, vol. 36, pp. 476-484, 2015.
Cunningham et al., "Serotonin at the Nexus of Impulsivity and Cue Reactivity in Cocaine Addiction," *Neuropharmacology* 76(0 0): 460-478.
International Search Report and Written Opinion of the International Searching Authority for International Application No. PCT/US2020/043103 dated Dec. 18, 2020 (12 pages).
International Search Report and Written Opinion of the International Searching Authority for International Application No. PCT/US2020/46212 dated Oct. 23, 2020 (10 pages).
International-type Search Report by International Searching Authority for SE1630067-5 dated Sep. 23, 2016 (18 pages).
Lashley et al. "Cortical a-synuclein load is associated with amyloid-b plaque burden in subset of Parkinson disease patients," Acta Neuropathol. 2008, 115, 417-425.
Vanover, Kimberly E. et al., "Pharmacological and Behavioral Profile of N-(4-Fluorophenylmethyl)-N-(1-methylpiperidin-4-yl)-N'-(4-(2-methylpropyloxy)phenylmethyl) Carbamide (2R,3R)-Dihydroxybutanedioate (2:1) (ACP-103), a Novel 5-Hydroxytryptamine$_{2A}$ Receptor Inverse Agonist," *The Journal of Pharmacology and Experimental Therapeutics* (2006) 317(2):910-918.
Weintraub et al., "Association of Dopamine Agonist Use With Impulse Control Disorders in Parkinson Disease," *Arch Neurol.* 2006 63(7):969-973.
Weintraub et al., "Clinical Spectrum of Impulse Control Disorders in Parkinson's Disease," *Movement Disorders 2015* 30(2):121-127.
Ye et al. "Improving response inhibition in Parkinson's disease with Atomoxetine." Biological Psychiatry, Apr. 15, 2015, 77, 740-748.

\* cited by examiner

PIMAVANSERIN ALONE OR IN COMBINATION FOR USE IN THE TREATMENT OF ALZHEIMER'S DISEASE PSYCHOSIS

CROSS REFERENCE TO RELATED APPLICATIONS

This application is a U.S. National Stage filing under 35 U.S.C. § 371 of International Application No. PCT/US2017/066340, Filed Dec. 14, 2017, which claims the benefit of priority of U.S. Provisional Application No. 62/436,959, filed Dec. 20, 2016 and U.S. Provisional Application No. 62/511,223, filed May 25, 2017. The disclosures of the above-referenced patent applications are hereby incorporated by reference in their entireties.

FIELD

Provided herein are methods for the treatment of Alzheimer's disease psychosis (hereafter, "ADP") which comprise the administration of pimavanserin.

BACKGROUND

Alzheimer's disease (AD) is a progressive neurodegenerative disorder. Its clinical features include cognitive dysfunction, memory abnormalities, progressive impairment in activities of daily living (ADL), and a host of behavioral and neuropsychiatric symptoms. (Cummings, *N. Eng. J. Med.,* 2004, vol. 351, 56-67.) While the diagnostic criteria for AD focus mostly on the related cognitive deficits, it is the behavioral and neuropsychiatric symptoms that are most troublesome for caregivers and lead to poor quality of life for patients. (Herrmann & Lanctot, *Can. J. Psychiatry,* 2007, vol. 52(10), 630-646.) These symptoms include agitation, aggressive behaviors, and psychosis.

There is no proven safe and effective treatment for moderate to severe ADP. Atypical antipsychotics are the only drug class for which there is robust clinical trial evidence for the treatment of ADP, with 18 randomized placebo controlled trials (RCTs) of up to 12 weeks duration. (Ballard et al., *Nat. Rev. Neurol,* 2009, vol. May 5 (5), 245-255.) Adverse effects related to antipsychotics in the same RCTs included sedation, parkinsonism, gait disturbances, peripheral edema, chest infections, pneumonia, thrombo-embolic events, stroke and death. None of the atypical antipsychotics has a licensed indication for the treatment of ADP. Current atypical antipsychotics are also associated with a statistically significant worsening of cognitive function in patients with Alzheimer's disease.

Additionally agitation is one of the most troublesome dementia symptoms. These verbal and physical behaviors can deviate from social norms and include irrelevant vocalizations, screaming, cursing, restlessness, wandering, strange movements, and handling things inappropriately. Such disruptive behaviors are a major source of stress and is time consuming for caregivers. In addition to psychosis, the detection, management, and treatment of agitation/aggression is important in the care of patients with dementia, such as AD patients.

Pimavanserin is a selective serotonin 5-HT2A inverse agonist. Pimavanserin has been approved by U.S. Food and Drug Administration (FDA) for the treatment of hallucinations and delusions associated with Parkinson's disease. Methods for the use of Pimavanserin are described in International Patent Publication WO 2004/064738 and U.S. Pat. Nos. 7,601,740; 7,659,285; 7,713,995; 7,732, 462; 7,994,193 and 8,008,323, the entirety of each of which is hereby incorporated by reference. Exemplary pharmaceutically acceptable salts of pimavanserin are described in International Patent Publication WO 2008/144326, U.S. Patent Publication Nos. 2006-0111399 and 2010-0305329, and International Patent Application PCT/US2016/42933, the entirety of each of which is incorporated herein by reference.

SUMMARY

Provided herein are methods for improving psychosis, such as hallucinations and delusions, in a patient, comprising administering pimavanserin, or a pharmaceutically acceptable salt thereof, to the patient, wherein the patient has Alzheimer's Disease.

Provided herein are methods for reducing psychosis, such as hallucinations and delusions, in a patient, comprising administering pimavanserin, or a pharmaceutically acceptable salt thereof, to the patient, wherein the patient has Alzheimer's Disease.

Also provided herein are methods of treating Alzheimer's disease psychosis in a patient as described above, wherein pimavanserin is administered in alternation or in combination with an anti-Alzheimer's agent.

Also provided herein are methods for improving sleep in a patient, comprising administering pimavanserin, or a pharmaceutically acceptable salt thereof, to the patient. In one embodiment, the patient is a possible or probably patient with Alzheimer's Disease. In one embodiment, the improvement of sleep is measured on the Neuropsychiatric Inventory—Nursing Home version (NPI-NH) Sleep/Nighttime Behavior subscale.

In some embodiments of the methods provided, delusions and/or hallucinations in a human with Alzheimer's Disease are treated.

Also provided herein are methods for reducing Neuropsychiatric Inventory—Nursing Home version (NPI-NH) score in a human with Alzheimer's Disease.

Also provided herein are methods for reducing agitated behavior or aggressive behavior in a human with dementia, such as Alzheimer's Disease.

Also provided herein are methods for reducing verbally agitated behavior or verbally aggressive behavior in a human with dementia.

In certain embodiments, the methods above comprise administering pimavanserin, or a pharmaceutically acceptable salt thereof to the human.

In certain embodiments, the human has a baseline score of 6 or greater in the Psychosis subscale (Domains A and B) of the NPI-NH or has a baseline score of 4 or greater in the Agitation/Aggression subscale (Domain C) of the NPI-NH.

In certain embodiments, the human has a baseline score of 12 or greater in the Psychosis subscale (Domains A and B) of the NPI-NH or has a baseline score of 6 or greater in the Agitation/Aggression subscale (Domain C) of the NPI-NH.

In certain embodiments, the human has a baseline score of 12 or greater in the Psychosis subscale (Domains A and B) of the NPI-NH.

In certain embodiments, the human has a baseline score of 6 or greater in the Agitation/Aggression subscale (Domain C) of the NPI-NH.

In certain embodiments, the patient has a baseline score of 12 or greater in the Psychosis subscale (Domains A and B) of the NPI-NH and has a baseline score of 6 or greater in the Agitation/Aggression subscale (Domain C) of the NPI-NH.

In certain embodiments, the Psychosis subscale of the NPI-NH is a combination of Delusions (Domain A) and Hallucinations (Domain B).

In certain embodiments, the effect of the treatment is determined by an improved patient score in the NPI-NH.

In certain embodiments, the effect of the agitated behavior and or aggressive behavior is determined by CMAI (Cohen-Mansfield Agitation Inventory) total score.

In certain embodiments, the effect of the treatment is determined by an improved patient score in the NPI-NH of at least 2, at least 3 or at least 4 points as compared to baseline score prior to administering pimavanserin.

In certain embodiments, the effect is determined by an improved patient score at least about 6 weeks from the initial administration of pimavanserin.

In certain embodiments, the effect is determined by an improved patient score about 6 weeks from the initial administration of pimavanserin.

In certain embodiments, the p-value of the improvement is between 0.0001 and 0.05.

In certain embodiments, a tartrate salt of pimavanserin is administered to the human.

In certain embodiments, the tartrate salt of pimavanserin is administered to the human orally.

In certain embodiments, the tartrate salt of pimavanserin is formulated for oral administration.

In certain embodiments, the tartrate salt of pimavanserin in an amount of about 0.001 mg to about 100 mg is administered to the patient.

In certain embodiments, pimavanserin in an amount of about 10 mg is administered to the patient.

In certain embodiments, pimavanserin in an amount of about 20 mg is administered to the patient.

In certain embodiments, the tartrate salt of pimavanserin in an amount of about 20 mg (equivalent to 17 mg pimavanserin) is administered to the patient.

In certain embodiments, the tartrate salt of pimavanserin in an amount of about 40 mg (equivalent to 34 mg pimavanserin) is administered to the patient.

In certain embodiments, the tartrate salt of pimavanserin is administered once, twice, or three times daily.

In certain embodiments, the tartrate salt of pimavanserin is administered once daily.

In certain embodiments, pimavanserin is administered during concomitant administration of an anti-Alzheimer's agent.

In certain embodiments, the anti-Alzheimer's agent is an acetylcholinesterase inhibitor.

In certain embodiments, the anti-Alzheimer's agent is selected from the group consisting of memantine, rivastigmine, tacrine, donepezil, verubecestat and galantamine.

In certain embodiments, the cognitive status of the human is not impaired.

In certain embodiments, the cognitive status is determined by the Mini-Mental State Examiner (MMSE) score.

In certain embodiments, the methods above further comprise steps of determining an baseline score on the NPI-NH for a human; and identifying a human with a score of 12 or greater in the Psychosis subscale (Domains A and B) of the NPI-NH prior to administering pimavanserin to the human.

In certain embodiments, the methods further comprise the steps of determining an baseline score on the NPI-NH for a human; and identifying a human with a score of 6 or greater in the Agitation/Aggression subscale (Domain C) of the NPI-NH prior to administering pimavanserin to the human.

Further aspects provided herein can be described according to the itemized list of embodiments below:

Item 1. A method for the treatment of Alzheimer's disease psychosis (hereafter, "ADP") comprising administrating pimavanserin, or a pharmaceutically acceptable salt thereof, to a patient, wherein the patient has Alzheimer's disease.

Item 2. A method for the treatment of hallucinations and/or delusions in a patient having Alzheimer's disease comprising administrating pimavanserin, or a pharmaceutically acceptable salt thereof, to a patient.

Item 3. The method of any one of items 1-3, wherein pimavanserin is orally administered in a daily dose of about 10, 17 or 34 mg.

Item 4. The method of any one of items 1-3, wherein the effect is determined by an improved patient score in the Neuropsychiatric Inventory-Nursing Home Version (NPI-NH) psychosis.

Item 5. The method of any one of items 1-4, wherein the NPI-NH psychosis is a combination of hallucinations and delusions domains.

Item 6. The method of any one of items 1-5, wherein the improvements in psychosis is at least 3 points, such as at least 3.2, such as at least 3.3, such as at least 3.4, such as at least 3.5, such as at least 3.6, such as at least 3.7, such as between 3.7 and 2.8 determined by NPI-NH psychosis scale.

Item 7. The method of any one of items 1-6, wherein the improvement is 1, 2, 3, 4, 5, 6, 7, 8, 9, 10, or 12 weeks from the initial daily administration of pimavanserin.

Item 8. The method of any one of items 1-7, wherein the p-value of the improvement is between 0.03 and 0.05, such as 0.04, such as 0.045, such as 0.0451.

Item 9. The method of any one of items 1-8, wherein the cognitive status of the patient is not impaired.

Item 10. The method of item 9, wherein the cognitive status is determined via Mini-Mental State Examiner (MMSE) score.

Item 11. The method of any one of items 1-10, wherein the effect is determined by an improved patient score in the Alzheimer's Disease Cooperative Study-Clinical Global Impression of Change (ADSC-CGIC).

Item 12. The method of any one of items 1-11, wherein the effect is determined by an improved patient score in the Agitation/Aggression subscale of NPI-NH.

Item 13. The method of any one of items 1-12, wherein the effect is determined by an improved patient score in the Sleep/Nighttime Behavior subscale of NPI-NH.

Item 14. The method of any one of items 1-13, wherein the effect is determined by an improved patient score in the Cohen-Mansfield Agitation Inventory-Short Form (CMAI-SF) or Cohen-Mansfield Agitation Inventory (CMAI) total score.

Item 15. The method of any one of items 1-14, wherein the effect is determined by an improved patient score in the aggressive behavior subdomain of CMAI-SF or CMAI.

Item 16. The method of any one of items 1-15, wherein the effect is determined by an improved patient score in the physically nonaggressive subdomain of CMAI-SF or CMAI.

Item 17. The method of any one of items 1-16, wherein the effect is determined by an improved patient score in the verbally aggressive subdomain of CMAI-SF or CMAI.

Item 18. The method of any one of items 1-17, wherein the patient is concurrently treated with an anti-Alzheimer's agent.

Item 19. The method of any one of items 1-18, wherein the anti-Alzheimer's agent is an acetylcholinesterase inhibitor.

Item 20. The method of any one of items 1-19, wherein the anti-Alzheimer's agent is selected from the group consisting of memantine, rivastigmine, tacrine, donepezil, verubecestat and galantamine Item 21. The method of any one of items 1-20, wherein the effect is determined by an improved patient score in the Alzheimer's Disease Cooperative Study—Activities of Daily Living Instrument (ADCS-ADL) total score.

Item 22. The method of any one of items 1-21, wherein the effect is determined by an improved patient score in the basic subdomain of ADCS-ADL.

Item 23. The method of any one of items 1-22, wherein the effect is determined by an improved patient score in the instrumental subdomain of ADCS-ADL.

Item 24. The method of any one of items 1-23, wherein the effect is an antipsychotic effect.

Item 25. A method for the treatment of delusions in a patient having Alzheimer's disease comprising administrating pimavanserin, or a pharmaceutically acceptable salt thereof, to a patient, wherein the patient has Alzheimer's disease.

Item 26. A method for the treatment of hallucinations in a patient having Alzheimer's disease comprising administrating pimavanserin, or a pharmaceutically acceptable salt thereof, to a patient, wherein the patient has Alzheimer's disease.

Item 27. A method for the improvement of a patient's score on the Neuropsychiatric Inventory Nursing Home Version (NPI-NH), comprising administering pimavanserin, or a pharmaceutically acceptable salt thereof, to the patient.

Item 28. A method for the reduction of psychosis in a patient having dementia, comprising administering pimavanserin, or a pharmaceutically acceptable salt thereof, to the patient.

Item 29 The method according to item 28, wherein the patient has Alzheimer's Disease.

Item 30. The method according to any one of items 27-29, wherein pimavanserin is administered daily to the patient and wherein the patient's NPI-NH score determined at about 4 weeks, about 5 weeks, about 6 weeks, about 7 or about 8 weeks after daily administration of pimavanserin is an improvement of at least 1.0, at least 2.0, at least 2.5, at least 3.0 or at least 4.0 as compared to the patient's score prior to being administered with pimavanserin.

Item 31. The method according to any one of items 27-30, wherein the pimavanserin is administered daily to the patient for at least 4, 5, 6, 7 or 8 weeks without any significant worsening of cognitive function as compared to prior to being administered with pimavanserin.

DETAILED DESCRIPTION

Figure 1:
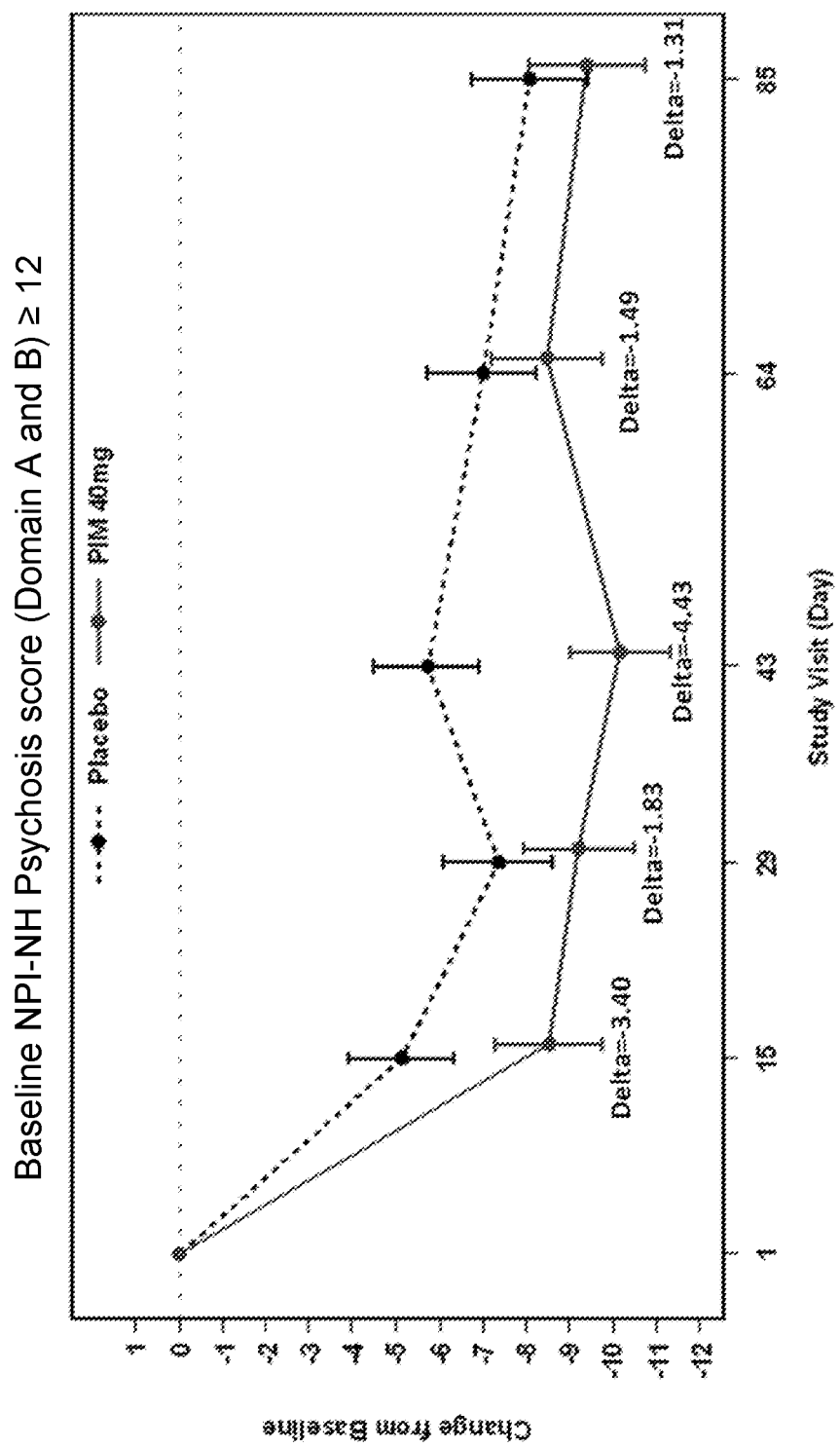
FIG. 1 depicts antipsychotic efficacy of pimavanserin in patients with Alzheimer's Disease that have a baseline NPI-NH Psychosis score (Domain A & B) of 12 or greater.
Figure 2:
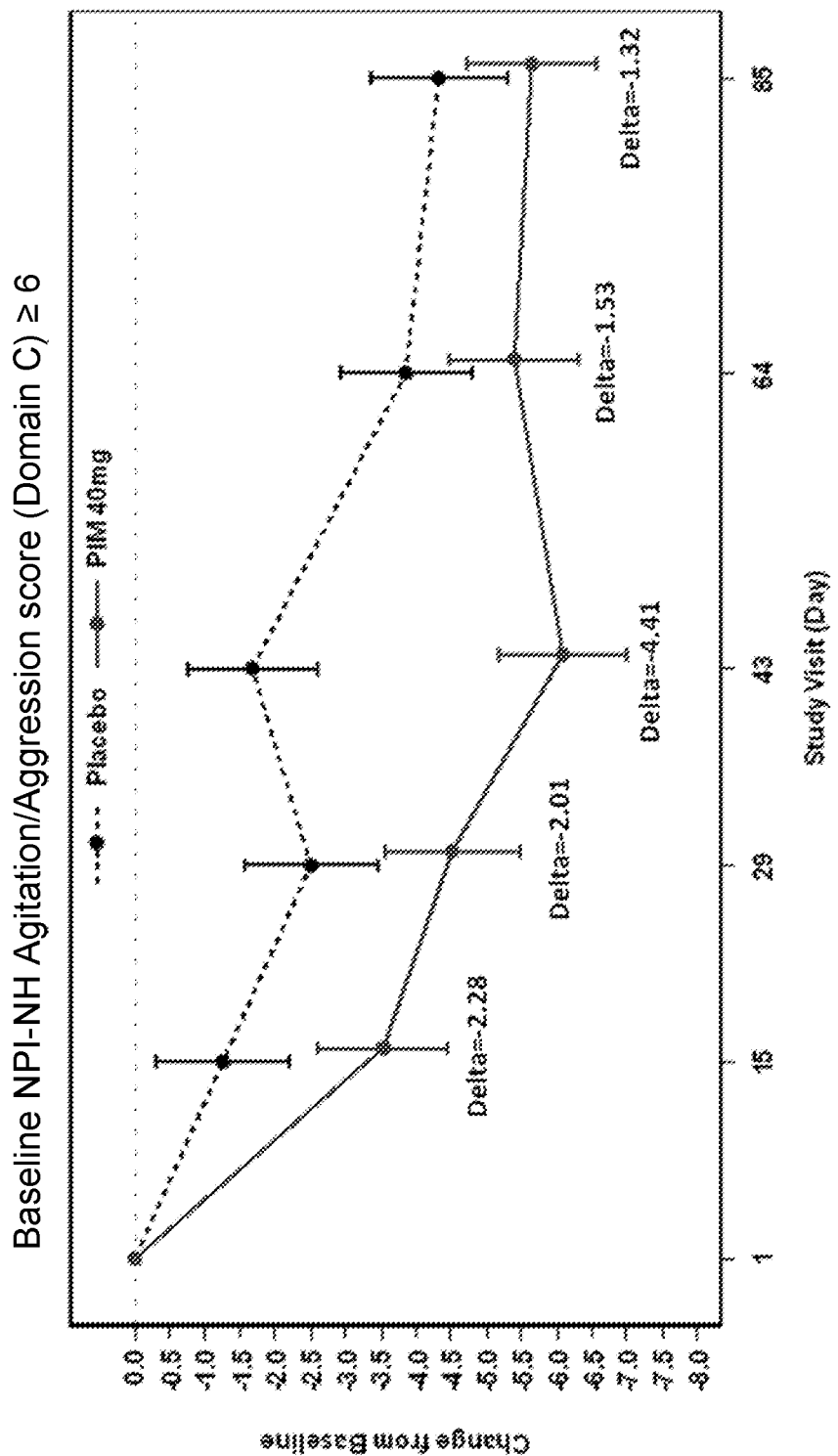
FIG. 2 depicts antipsychotic efficacy of pimavanserin in patients with Alzheimer's Disease that have a baseline NPI-NH Agitation/Aggression score (Domain C) of 6 or greater.
Figure 3:
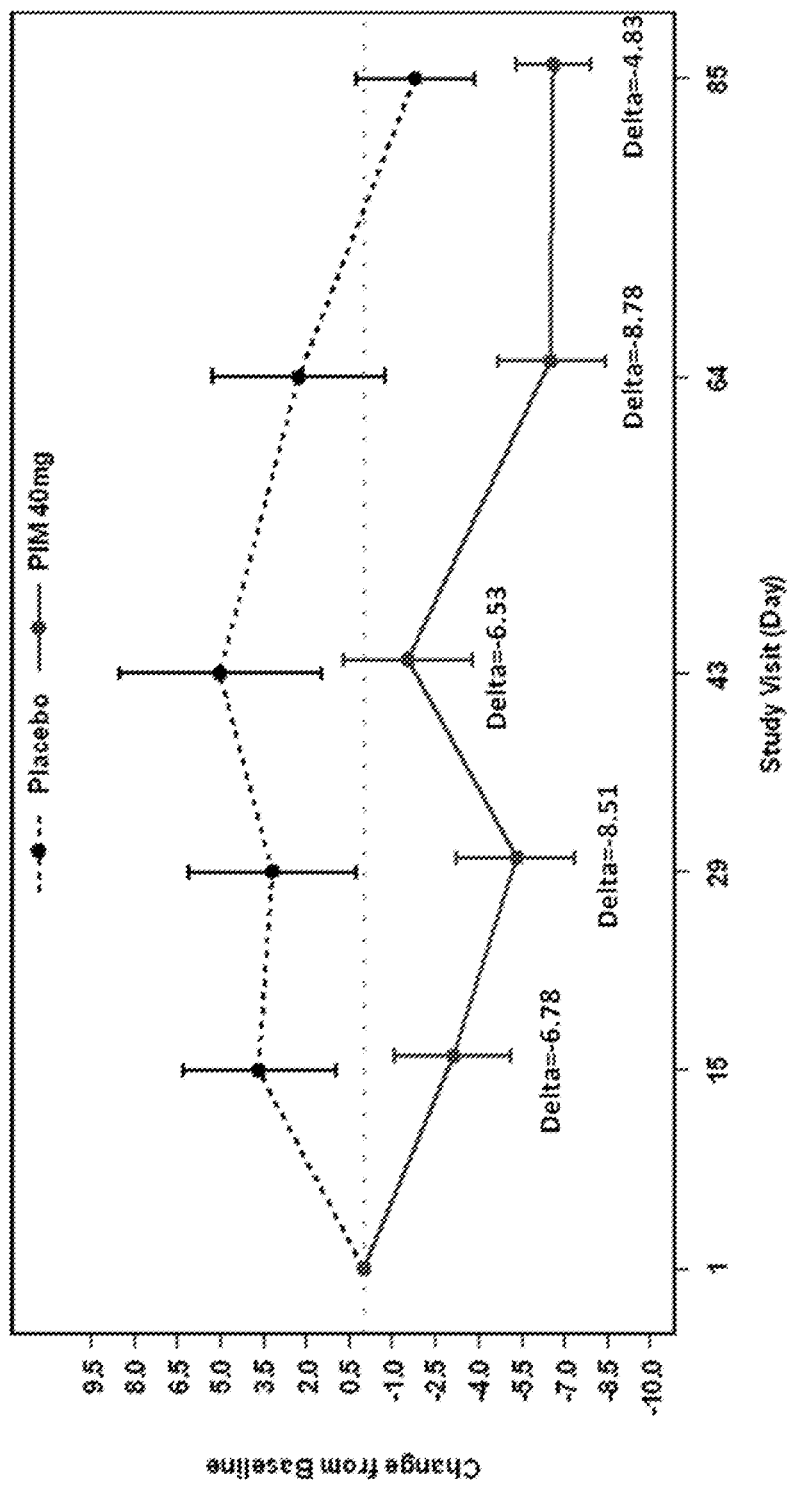
FIG. 3 depicts antipsychotic efficacy of pimavanserin in patients with Alzheimer's Disease that had antipsychotic use prior to the baseline measurement of the NPI-NH on day 0.

Provided herein are methods for the treatment of Alzheimer's disease psychosis comprising administration of pimavanserin to a patient. Also provided herein are methods of treating Alzheimer's disease psychosis in a patient as described above, wherein pimavanserin is administered in alternation or in combination with an anti-Alzheimer's agent.

Also provided herein are methods of inducing a rapid or early onset of an antipsychotic effect in a patient suffering from ADP, comprising administering pimavanserin to a subject suffering from ADP such that there is a rapid or early onset of an antipsychotic effect. In one embodiment, rapid or early onset of an antipsychotic effect is measured as compared to conventional therapies for ADP, such as the administration of an antipsychotic agent, such as an atypical antipsychotic. Exemplary agents used for the treatment of ADP include, but are not limited to, memantine, cholinesterase inhibitors, tacrine, donepezil, and rivastigmine.

Also provided herein are methods for the treatment of Alzheimer's disease psychosis comprising diagnosing a patient to have ADP, and administrating pimavanserin to the patient. In one embodiment, the patient is diagnosed to have psychotic symptoms. In another embodiment, the psychotic symptoms include hallucinations, such as visual and/or visual auditory hallucinations, and/or delusions. Provided herein are also methods of treating hallucinations and/or delusions in a patient diagnosed with Alzheimer's disease.

Also provided herein are methods for the treatment of psychosis, or a symptom thereof, in a human with Alzheimer's Disease.

Also provided herein are methods for the treatment of delusions and/or hallucinations in a human with Alzheimer's Disease.

Also provided herein are methods for reducing NPI-NH score in a human with Alzheimer's Disease.

Also provided herein are methods for the reducing agitated behavior and/or aggressive behavior in a human with dementia, e.g. wherein the human has a diagnosis of probable Alzheimer's Disease according to the National Institute on Aging-Alzheimer's Association (NIA-AA) guidelines.

Also provided herein are methods for the reducing agitated behavior and/or aggressive behavior in a human with probable Alzheimer's Disease, and wherein the agitated behavior and/or aggressive behavior is one or more of the following pacing and aimless wandering, such as constantly walking back and forth; inappropriate dressing or disrobing, such as putting on too many clothes, putting on clothing in a strange manner (e.g. putting pants on head), taking off clothing in public; spitting, such as spitting onto floor, and other people; cursing or verbal aggression, such as using words; swearing, use of obscenity, profanity, unkind speech or criticism, verbal anger, verbal combativeness; constant unwarranted request for attention or help, such as verbal or nonverbal unreasonable nagging, pleading, demanding; repetitive sentences or questions, such as repeating the same sentence or question one right after the other; hitting, such as physical abuse, striking others, pinching others, banging self/furniture; kicking, such as strike forcefully with feet at people or objects; grabbing onto people or things inappropriately, such as snatching, seizing roughly, taking firmly, or yanking; pushing, such as forcefully thrusting, shoving, moving putting pressure against; throwing things, such as hurl, violently tossing up in air, tipping off surfaces, flinging, intentionally spilling food; making strange noises, such as including crying, weeping, moaning, weird laughter, grinding teeth; screaming, such as loud shrill, shouting, piercing howl; biting, such as chomp, gnash, gnaw; scratching, such as clawing, scraping with fingernails; trying to get to a different place, such as trying to get out of the building, off the property, leaving inappropriately, trying to get into locked areas, trespassing within unit, into offices, other resident's room or closet; intentional falling, such as purposefully falling onto floor, include from wheelchair, chair, or bed; complaining—whining, complaining about self, somatic complaints, personal gripes or complaining about external things or other people; negativism, such as bad attitude, doesn't like anything, nothing is right; eating or drinking inappropriate substances, such as putting into mouth and trying to swallow items that are inappropriate; hurting self or other, such as burning self or other, cutting self or other, touching self or other with harmful objects; handling things inappropriately, such as picking up things that don't belong to them, rummaging through drawers, moving furniture, playing with food, fecal smearing; hiding things, such as putting objects under or behind something; hoarding things, such as putting many or inappropriate objects in purse or pockets, keeping too many of an item; tearing things or destroying property, such as shredding, ripping, breaking, stomping on something; performing repetitious mannerisms, such as stereotypic movement, such as patting, tapping, rocking self, fiddling with something, twiddling with something, rubbing self or object, sucking fingers, taking shoes on and off, picking at self, clothing, or objects, picking imaginary things out of air or off floor, manipulation of nearby objects in a repetitious manner; making verbal sexual advances, such as sexual propositions, sexual innuendo, or "dirty" talk; making physical sexual advances or exposing genitals, such as touching a person in an inappropriate sexual way, rubbing genital area, inappropriate masturbation, when not alone in own room or bathroom, unwanted fondling or kissing; and general restlessness—fidgeting, always moving around in seat, getting up and sitting down inability to sit still.

Also provided herein are methods for reducing verbally agitated behavior or verbally aggressive behavior in a human with dementia.

In certain embodiments, the methods above comprise administering pimavanserin, or a pharmaceutically acceptable salt thereof to the human.

In certain embodiments, the methods above further comprise steps of determining a baseline score on the NPI-NH for a human; and identifying a human with a score of 12 or greater in the Psychosis subscale (Domains A and B) of the NPI-NH prior to administering pimavanserin to the human.

In certain embodiments, the methods further comprise the steps of determining a baseline score on the NPI-NH for a human; and identifying a human with a score of 6 or greater in the Agitation/Aggression subscale (Domain C) of the NPI-NH prior to administering pimavanserin to the human.

In an embodiment, pimavanserin is administered orally.

In an embodiment, pimavanserin or a pharmaceutically acceptable salt thereof is administered. In another embodiment, pimavanserin tartrate salt is administered.

In an embodiment, pimavanserin is orally administered in a daily dose of about 10-60 mg. In another embodiment, pimavanserin tartrate is orally administered in a daily dose of about 40 mg. In some embodiments, the daily dose is 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, or 60 mg. In an embodiment the daily dose of pimavanserin tartrate is administered once, twice or three times per day, for example a 40 mg dose of pimavanserin tartrate is administered once a day, or 20 mg pimavanserin tartrate is administered twice a day.

In another embodiment, pimavanserin is orally administered in a daily dose of about 34 mg. In some embodiments, the daily dose is 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, or 60 mg. In an embodiment the daily dose of pimavanserin is administered once, twice or three times per day, for example a 34 mg dose of pimavanserin is administered once a day, or 17 mg pimavanserin is administered twice a day, or a 10 mg dose pimavanserin is administered twice a day.

In an embodiment, the tartrate salt of pimavanserin is formulated for oral administration. In another embodiment, the tartrate salt of pimavanserin in an amount of about 20 mg (equivalent to 17 mg pimavanserin) is administered. In yet another embodiment, the tartrate salt of pimavanserin in an amount of about 40 mg (equivalent to 34 mg pimavanserin) is administered. In yet another embodiment, pimavanserin in an amount of about 20 mg is administered. In yet another embodiment, pimavanserin in an amount of about 10 mg is administered.

In an embodiment, the tartrate salt of pimavanserin is administered once, twice, or three times daily. In an embodiment, the tartrate salt of pimavanserin is administered twice daily. In an embodiment, the tartrate salt of pimavanserin is administered once daily.

In an embodiment, pimavanserin is administered during concomitant administration of an anti-Alzheimer's agent. In another embodiment, the anti-Alzheimer's agent is an acetylcholinesterase inhibitor. In yet another embodiment, the anti-Alzheimer's agent is selected from the group consisting of memantine, rivastigmine, tacrine, donepezil, verubecestat and galantamine.

In an embodiment, the method comprises the oral administration of pimavanserin, or a pharmaceutically acceptable salt thereof, to a patient with Alzheimer's disease psychosis, wherein the administration results in an antipsychotic effect.

In some embodiments, pimavanserin is administered each day for at least 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks or 15 weeks. In an embodiment, pimavanserin is administered twice daily to meet the daily dose. In another embodiment, pimavanserin is administered twice daily for at least 3 weeks to meet the daily dose. In an embodiment, pimavanserin tartrate is administered once daily to meet the daily dose (e.g. a 40 mg daily dose is administered once daily). In another embodiment, pimavanserin tartrate is administered once daily for at least 3 weeks to meet the daily dose. In an embodiment, a 40 mg daily dose is administered in 20 mg twice daily. In another embodiment, a 40 mg daily dose is administered once daily.

It will be understood that in certain embodiments of the methods provided herein, a patient is a human.

In an embodiment, the cognitive status of the human is not impaired. In another embodiment, the cognitive status of the human is not impaired, and determined by the Mini-Mental State Examiner (MMSE) score.

In one embodiment, the age of the patient is 45 years or older, 50 years or older, or 55 years or old, or 60 years or older, or 65 years or older, or 70 years or older at baseline. In another embodiment, the age of the patient is 50 years or older.

In one embodiment, the patient is a possible or probable patient with Alzheimer's disease defined by the National Institute of Neurological and Communicative Disorders and Stroke-Alzheimer's Disease and Related Disorders Association (NINCDS-ADRDA).

In one embodiment, the age of the patient is 50 years or older and the patient is a possible or probable patient with Alzheimer's disease defined by the National Institute of Neurological and Communicative Disorders and Stroke-Alzheimer's Disease and Related Disorders Association (NINCDS-ADRDA).

In some embodiments, the symptoms of Alzheimer's disease include psychosis (e.g., delusions and/or hallucinations), anxiety, depression, dementia including lewy body dementia and vascular dementia, episodic memory impairment, agitation and aggressions, stress, weight loss, seizures, and motor function.

In some embodiments, administration of pimavanserin results in an early onset of one or more efficacious effects. In some embodiments, the efficacious effect is the reduction of psychotic symptoms. In some embodiments, the efficacious effect is the antipsychotic effect.

In an embodiment, the effect is determined by the Neuropsychiatric Inventory-Nursing Home Version (NPI-NH) psychosis scale.

In an embodiment, the effect of administration of pimavanserin to a human diagnosed with dementia on agitated and/or aggressive behavior is determined by the Neuropsychiatric Inventory-Nursing Home Version (NPI-NH) agitation/aggression scale.

The NPI-NH was developed to assess psychopathology in patients with dementia in nursing homes and evaluates. The nursing home version of this scale was designed to examine psychopathology in nursing home patients and has been validated for use in this population. (Wood et al., *Am. J. Geriatr. Psychiatr.*, 2000, vol. 8(1), 75-83.)

TABLE 1

Domains of Neuropsychiatric Inventory Nursing Home Version (NPI-NH)

Behavioral Domains

| Delusions (Domain A) | Hallucinations (Domain B) | Agitation/Aggression (Domain C) |
|---|---|---|
| Anxiety (Domain E) | Elation/Euphoria (Domain F) | Depression/dysphoria (Domain D) |
| Apathy/Indifference (Domain G) | Disinhibition (Domain H) | Irritability/lability (Domain I) |
| Aberrant motor behavior (Domain J) | | |

Neurovegetative Changes Domains

| Sleep and nighttime behavior disorders (Domain K) | Eating disorders (Domain L) |
|---|---|

The NPI-NH includes ten behavioral domains and two neurovegetative changes domains. As shown in Table 1, the behavioral domains are delusions (Domain A), hallucinations (Domain B), agitation/aggression (Domain C), depression/dysphoria (Domain D), anxiety (Domain E), elation/euphoria (Domain F), apathy/indifference (Domain G), disinhibition (Domain H), irritability/lability (Domain I), and aberrant motor behavior (Domain J). The neurovegetative changes domains are sleep and nighttime behavior disorders (Domain K) and appetite and eating disorders (Domain L). (Wood et al., *Am. J. Geriatr. Psychiatr.*, 2000, vol. 8(1), 75-83).

The NPI-NH is based on responses from an informed professional caregiver involved in the daily care of the resident. The interview is best conducted in the absence of the resident to facilitate an open discussion of behaviors that may be difficult to describe with the resident present.

To determine the score for a given domain, the caregivers rate frequency and severity of the resident's behavior for that particular domain. The frequency is rated on a 0-4 point scale. For example, the frequency is rated as a) 0 for not present; b) 1 for occasional; c) 2 for often; d) 3 for frequent; and e) 4 for very frequent occurrence of the behavior in question. The severity is rated on a 1-3 point scale. For example, the severity is rated as a) 1 for mild; b) 2 for moderate; and 3 for severe. The score of each domain is determined by multiplying the frequency rating score by the severity rating score. The score of each domain ranges from 0 to 12.

A total NPI-NH score can be calculated by adding all of the ten behavioral domain scores together.

A psychosis score on the psychosis subscale is the total score of the score of delusions (Domain A) and hallucinations (Domain B). For example, when the delusions score (Domain A) is 4 and the hallucinations score (Domain B) is 6, the psychosis score is 10. The psychosis score typically ranges from 0 to 24.

In an embodiment, the human has a baseline score of 3 or greater, 4 or greater, 5 or greater, 6 or greater, 7 or greater, 8 or greater, 9 or greater, 10 or greater, 11 or greater, 12 or greater, 13 or greater, 14 or greater, 15 or greater, or 16 or greater in the psychosis sub scale (Domains A and B) of the NPI-NH. In another embodiment, the human has a baseline score of 6 or greater in the psychosis subscale (Domains A and B) of the NPI-NH. In yet another embodiment, the human has a baseline score of 9 or greater in the psychosis subscale (Domains A and B) of the NPI-NH. In yet another embodiment, the human has a baseline score of 12 or greater in the psychosis subscale (Domains A and B) of the NPI-NH.

In an embodiment, the human has a baseline score of 3 or greater, 4 or greater, 5 or greater, 6 or greater, 7 or greater, or 8 or greater in the agitation and aggression subscale (Domain C) of the NPI-NH. In another embodiment, the human has a baseline score of 3 or greater, 4 or greater, 5 or greater, 6 or greater, 7 or greater, or 8 or greater in the depression/dysphoria subscale (Domain D) of the NPI-NH. In yet another embodiment, the human has a baseline score of 3 or greater, 4 or greater, 5 or greater, 6 or greater, 7 or greater, or 8 or greater in the anxiety subscale (Domain E) of the NPI-NH. In yet another embodiment, the human has a baseline score of 3 or greater, 4 or greater, 5 or greater, 6 or greater, 7 or greater, or 8 or greater in the elation/euphoria subscale (Domain F) of the NPI-NH. In yet another embodiment, the human has a baseline score of 3 or greater, 4 or greater, 5 or greater, 6 or greater, 7 or greater, or 8 or greater in the apathy/indifference subscale (Domain G) of the NPI-NH. In yet another embodiment, the human has a baseline score of 3 or greater, 4 or greater, 5 or greater, 6 or greater, 7 or greater, or 8 or greater in the disinhibition subscale (Domain H) of the NPI-NH. In yet another embodiment, the human has a baseline score of 3 or greater, 4 or greater, 5 or greater, 6 or greater, 7 or greater, or 8 or greater in the disinhibition subscale (Domain H) of the NPI-NH. In yet another embodiment, the human has a baseline score of 3 or greater, 4 or greater, 5 or greater, 6 or greater, 7 or greater, or 8 or greater in the irritability/lability subscale (Domain I)

of the NPI-NH. In yet another embodiment, the human has a baseline score of 3 or greater, 4 or greater, 5 or greater, 6 or greater, 7 or greater, or 8 or greater in the sleep and nighttime behavior disorders subscale (Domain J) of the NPI-NH. In yet another embodiment, the human has a baseline score of 3 or greater, 4 or greater, 5 or greater, 6 or greater, 7 or greater, or 8 or greater in the sleep and nighttime behavior disorders subscale (Domain K) of the NPI-NH. In yet another embodiment, the human has a baseline score of 3 or greater, 4 or greater, 5 or greater, 6 or greater, 7 or greater, or 8 or greater in the appetite and eating disorders subscale (Domain L) of the NPI-NH.

In an embodiment, the human has a baseline score of 6 or greater in the psychosis sub scale (Domains A and B) of the NPI-NH; and/or has a baseline score of 3 or greater in the agitation and aggression subscale (Domain C) of the NPI-NH. In another embodiment, the human has a baseline score of 6 or greater in the psychosis subscale (Domains A and B) of the NPI-NH; and/or has a baseline score of 6 or greater in the agitation and aggression sub scale (Domain C) of the NPI-NH. In yet another embodiment, the human has a baseline score of 6 or greater in the psychosis subscale (Domains A and B) of the NPI-NH; and/or has a baseline score of 9 or greater in the agitation and aggression subscale (Domain C) of the NPI-NH. In yet another embodiment, the human has a baseline score of 9 or greater in the psychosis subscale (Domains A and B) of the NPI-NH; and/or has a baseline score of 3 or greater in the agitation and aggression subscale (Domain C) of the NPI-NH. In yet another embodiment, the human has a baseline score of 9 or greater in the psychosis subscale (Domains A and B) of the NPI-NH; and/or has a baseline score of 6 or greater in the agitation and aggression subscale (Domain C) of the NPI-NH. In yet another embodiment, the human has a baseline score of 9 or greater in the psychosis subscale (Domains A and B) of the NPI-NH; and/or has a baseline score of 9 or greater in the agitation and aggression subscale (Domain C) of the NPI-NH. In yet another embodiment, the human has a baseline score of 12 or greater in the psychosis subscale (Domains A and B) of the NPI-NH; and/or has a baseline score of 3 or greater in the agitation and aggression subscale (Domain C) of the NPI-NH. In yet another embodiment, the human has a baseline score of 12 or greater in the psychosis subscale (Domains A and B) of the NPI-NH; and/or has a baseline score of 6 or greater in the agitation and aggression subscale (Domain C) of the NPI-NH. In yet another embodiment, the human has a baseline score of 12 or greater in the psychosis subscale (Domains A and B) of the NPI-NH; and/or has a baseline score of 9 or greater in the agitation and aggression subscale (Domain C) of the NPI-NH.

In an embodiment, the human has no history of being prescribed for using an anti-psychotic agent. In another embodiment, the human has a baseline score of 12 or greater in the psychosis subscale (Domains A and B) of the NPI-NH and/or has no history being prescribed for using an anti-psychotic agent. In yet another embodiment, the human has a baseline score of 6 or greater in the agitation and aggression subscale (Domain C) of the NPI-NH and/or has no history of being prescribed for using an anti-psychotic agent. In yet another embodiment, the human has a baseline score of 12 or greater in the psychosis sub scale (Domains A and B) of the NPI-NH; has a baseline score of 6 or greater in the agitation and aggression subscale (Domain C) of the NPI-NH; and/or has no history of being prescribed for using an anti-psychotic agent.

In certain embodiments, the verbally agitated behavior and/or verbally aggressive behavior includes, but is not limited to, shouting, screaming, swearing, making verbal sexual advances, cursing or verbal aggression, repetitive sentences or questions, making strange noises (weird laughter or crying), complaining, negativism, constant unwarranted request for attention or help, and making threats.

In some embodiments, an "improvement" refers to a reduction of score on the scale or subscale of the Neuropsychiatric Inventory-Nursing Home Version (NPI-NH), the Alzheimer's Disease Cooperative Study-Clinical Global Impression of Change (ADSC-CGIC), the Cohen-Mansfield Agitation Inventory (CMAI) or the Cohen-Mansfield Agitation Inventory-Short Form (CMAI-SF). For example, an improvement refers to a reduction of a patient's total NPI-NH score from a score of 50 to a score of 40. In some embodiments, the improvement may optionally refer to one or more patients.

In certain embodiments, the effect is determined by an improved score in the NPI-NH. In certain embodiments, the improved score in the NPI-NH is at least 2, at least 3, at least 4, at least 5, at least 6, at least 7, at least 8, or at least 9 points as compared to baseline score prior to administering pimavanserin. In certain embodiments, the improved score in the NPI-NH is at least 2, at least 3, or at least 4 points as compared to baseline score prior to administering pimavanserin.

In certain embodiments, the improved score in the psychosis subscale (Domains A and B) of the NPI-NH is at least 2, at least 3, at least 4, at least 5, at least 6, at least 7, at least 8, or at least 9 points as compared to baseline score prior to administering pimavanserin. In certain embodiments, the improved score in the psychosis subscale (Domains A and B) of the NPI-NH is at least 2, at least 3, or at least 4 points as compared to baseline score prior to administering pimavanserin.

In certain embodiments, the methods provided herein reduce the patient's NPI-NH score by at least 2, at least 3, at least 4, at least 5, at least 6, at least 7, at least 8, or at least 9 points as compared to baseline score prior to administering pimavanserin. In certain embodiments, the methods provided herein reduce the patient's NPI-NH score by at least 2, at least 3, or at least 4 points as compared to baseline score prior to administering pimavanserin.

In certain embodiments, the methods provided herein reduce the patient's score in the psychosis subscale (Domains A and B) of the NPI-NH by at least 2, at least 3, at least 4, at least 5, at least 6, at least 7, at least 8, or at least 9 points as compared to baseline score prior to administering pimavanserin. In certain embodiments, the methods provided herein reduce the patient's score in the psychosis subscale (Domains A and B) of the NPI-NH by at least 2, at least 3, or at least 4 points as compared to baseline score prior to administering pimavanserin.

One of ordinary skills in the art will understand that the improved score or the points of score reduced will be less than the baseline score.

In certain embodiments, the effects is determined by an improved score at least about 4 weeks, at least about 5 weeks, at least about 6 weeks, at least about 7 weeks, or at least about 8 weeks from the initial administration of pimavanserin. In certain embodiments, the effects is determined about 4 weeks, about 5 weeks, about 6 weeks, about 7 weeks, about 8 weeks, about 9 weeks, about 10 weeks, about 11 weeks, or about 12 weeks from the initial administration of pimavanserin. In certain embodiments, the effects is determined about 6 weeks from the initial administration of pimavanserin.

In certain embodiments, the p-value of the improvement is between 0.0001 and 0.05.

In some embodiments, provided herein are methods for the improvement of a patient's score on the Neuropsychiatric Inventory Nursing Home Version (NPI-NH), comprising administering pimavanserin, or a pharmaceutically acceptable salt thereof, to the patient.

In some embodiments the improvement in NPI-NH is determined at about 3-9 weeks, or about 4 weeks, about 5 weeks, about 6 weeks, about 7 or about 8 weeks, of daily administration of pimavanserin.

In certain embodiments of the methods provided herein, the improvement in NPI-NH score is an improvement of between 1.0 to 4.0, or at least 1.0, at least 1.5, at least 2.0, at least 2.5, at least 3.0 or at least 3.5, or at least 4.0 as compared to the patient's score prior to being administered with pimavanserin. The improvement can be an improvement in a total NPI score, or, for example, can be an improvement in one NPI domain, or across one, or two, or three NPI domains.

In certain embodiment of the methods provided herein, pimavanserin is administered to a patient chronically, for example for at least 4, 5, 6, 7, 8, 9, 10, 11, 12, or more weeks, without any significant worsening of cognitive function as compared to prior to being administered with pimavanserin. Cognitive function can, for example, be assessed using any technique known to this skilled in the art, or can be assessed, for instance, as described elsewhere in this specification.

In another embodiment, the effect is determined by an improved patient score in the Alzheimer's Disease Cooperative Study—Clinical Global Impression of Change (ADSC-CGIC). ADCS-CGIC scale allows the Investigator to determine the patient's overall clinical condition as it relates to their psychosis and neuropsychiatric symptoms and to address the clinical significance of changes from Baseline in other psychometric measures. (Schneider et al., *Alzheimer's Disease and Associated Disorders*, 1997, vol. 11(2), S22-S32.)

In one embodiment, the effect is determined by an improved patient score in the Delusions and Hallucinations subscale of NPI-NH (Domain A and B). In another embodiment, the antipsychotic effect is determined by an improved patient score in the Agitation/Aggression subscale of NPI-NH (Domain C). In one embodiment, the antipsychotic effect is determined by an improved patient score in the Sleep/Nighttime Behavior subscale of NPI-NH (Domain K).

In one embodiment, the effect is determined by an improved patient score in the Cohen-Mansfield Agitation Inventory-Short Form (CMAI-SF) total score. The CMAI-SF is a 14-item instrument assessing frequency of manifestations of agitation in the elderly based on directly observable behaviors (Werner et al., *Geriatric Nursing*, 1994, vol. 15(3), 142-146; Koss et al., *Alzheimer's Disease and Associated Disorders*, 1997, vol. 11, 45-50) including physically aggressive behaviors and verbally aggressive behaviors. (Cohen-Mansfield et al., *J of Gerontology Med. Sci.*, 1989, vol. 44(3), M77-M84; Werner et al., *Geriatric Nursing*, 1994, vol. 15(3), 142-146; Koss et al., *Alzheimer's Disease and Associated Disorders*, 1997, vol. 11, 45-50.) In another embodiment, the effect is determined by an improved patient score in the aggressive behavior subdomain of CMAI-SF. In one embodiment, the effect is determined by an improved patient score in the physically nonaggressive subdomain of CMAI-SF. In another embodiment, the antipsychotic effect is determined by an improved patient score in the verbally aggressive subdomain of CMAI-SF.

In one embodiment, the effect on agitated and/or aggressive behavior is determined by an improved patient score in the Cohen-Mansfield Agitation Inventory (CMAI) total score. The CMAI is a 14- or 28-item instrument assessing frequency of manifestations of agitation in the elderly based on directly observable behaviors (Werner et al., *Geriatric Nursing*, 1994, vol. 15(3), 142-146; Koss et al., *Alzheimer's Disease and Associated Disorders*, 1997, vol. 11, 45-50) including physically aggressive behaviors and verbally aggressive behaviors. (Cohen-Mansfield et al., *J of Gerontology Med. Sci.*, 1989, vol. 44(3), M77-M84; Werner et al., *Geriatric Nursing*, 1994, vol. 15(3), 142-146; Koss et al., *Alzheimer's Disease and Associated Disorders*, 1997, vol. 11, 45-50.) In another embodiment, the effect is determined by an improved patient score in the aggressive behavior subdomain of CMAI. In one embodiment, the effect is determined by an improved patient score in the physically nonaggressive subdomain of CMAI. In another embodiment, the antipsychotic effect is determined by an improved patient score in the verbally aggressive subdomain of CMAI.

In one embodiment, the effect is determined by an improved patient score in the Alzheimer's Disease Cooperative Study—Activities of Daily Living Instrument (ADCS-ADL) total score. The ADCS-ADL is an inventory to assess activities of daily living in patients with AD. (Galasko et al., *Alzheimer's Disease and Associated Disorders*, 1997, vol. 11(2), S33-S39.) This is a caregiver-rated questionnaire that includes 23 items related to patient ADLs. The instrument assesses functional capacity across a large spectrum of dementia severity. In one embodiment, the antipsychotic effect is determined by an improved patient score in the basic subdomain of ADCS-ADL. In another embodiment, the effect is determined by an improved patient score in the instrumental subdomain of ADCS-ADL.

In some embodiments the effect of the treatment is an antipsychotic effect, for example determined by one or more of the following: an improved patient score in the Neuropsychiatric Inventory-Nursing Home Version (NPI-NH) psychosis scale, an improved patient score in the Alzheimer's Disease Cooperative Study—Clinical Global Impression of Change (ADSC-CGIC), an improved patient score in the Delusions and Hallucinations sub scale of NPI-NH (Domain A and B), an improved patient score in the aggressive behavior subdomain of CMAI or CMAI-SF, or an improved patient score in the Alzheimer's Disease Cooperative Study—Activities of Daily Living Instrument (ADCS-ADL) total score.

In some embodiments the effect of the treatment is an antipsychotic effect, for example determined by an improved patient score in the Neuropsychiatric Inventory-Nursing Home Version (NPI-NH) psychosis scale, without impairing cognition, as determined by Mini-Mental State Examiner (MMSE) score. In some embodiment the antipsychotic effect without impairing cognition is determined over the 12 weeks of treatment. The MMSE is a brief 30-point questionnaire that is used to quantitatively assess cognition (Folstein et al., *Journal of Psychiatric Research.* 12 (3): 189-98, 1975). The MMSE test includes simple questions and problems in a number of areas: the time and place of the test, repeating lists of words, arithmetic, language use and comprehension, and copying a drawing. It can be used to screen for cognitive impairment, to estimate the severity of cognitive impairment at a given point in time, to follow the course of cognitive changes in an individual over time, and to document an individual's response to treatment.

Also provided herein is a method for the improvement of sleep in an Alzheimer's disease patient, comprising the oral administration of pimavanserin, or a pharmaceutically acceptable salt thereof. In one embodiment, the improvement of sleep is measured on the NPI-NH Sleep/Nighttime Behavior subscale (Domain K).

In one embodiment, provided herein is a method for the improvement of sleep in a Alzheimer's disease patient, comprising the oral administration of pimavanserin, or a pharmaceutically acceptable salt thereof, to the patient in a daily dose of about 34 mg, wherein the improvement of sleep is measured on the NPI-NH Sleep/Nighttime Behavior subscale (Domain K). In another embodiment, the method is for the improvement of frequency of nighttime behavior by the NPI-NH Sleep/Nighttime Behavior subscale (Domain K). In one embodiment, the method is for the improvement of severity of nighttime behavior by the NPI-NH Sleep/Nighttime Behavior subscale (Domain K). In another embodiment, the method is for the improvement of occupational disruptiveness of nighttime behavior by the NPI-NH Sleep/Nighttime Behavior subscale (Domain K).

Also provided herein are methods of treating Alzheimer's disease psychosis in a patient as described above, wherein pimavanserin is administered in alternation or in combination with an anti-Alzheimer's agent. In some embodiments, the patient is concurrently treated with an anti-Alzheimer's agent. In some embodiments, the anti-Alzheimer's agent is selected from the group consisting acetylcholinesterase inhibitors, such rivastigmine, tacrine, donepezil and galantamine. In some embodiments, the anti-Alzheimer's agent is selected from the group consisting of memantine, rivastigmine, tacrine, donepezil, verubecestat and galantamine.

Provided herein are methods for the treatment of psychosis (e.g. hallucinations and/or delusions), or a symptom thereof, in a human with Alzheimer's Disease comprising coadministering to the human pimavanserin, or a pharmaceutically acceptable salt thereof, and a Selective Serotonin Reuptake Inhibitor (SSRI), wherein the human:

has a baseline score of 6 or greater in the Psychosis subscale (Domains A and B) of the Neuropsychiatric Inventory-Nursing Home Version (NPI-NH); or has a baseline score of 4 or greater in the Agitation/Aggression subscale (Domain C) of the NPI-NH.

In some embodiments the human has a baseline score of 12 or greater in the Psychosis subscale (Domains A and B) of the NPI-NH; or has a baseline score of 6 or greater in the Agitation/Aggression subscale (Domain C) of the NPI-NH.

Provided herein are methods for reducing verbally agitated behavior or verbally aggressive behavior in a human with dementia comprising coadministering to the human pimavanserin, or a pharmaceutically acceptable salt thereof and a Selective Serotonin Reuptake Inhibitor (SSRI) to the human, wherein the human:

has a baseline score of 6 or greater in the Psychosis subscale (Domains A and B) of the NPI-NH; or has a baseline score of 4 or greater in the Agitation/Aggression subscale (Domain C) of the NPI-NH. In certain embodiments, the human is for example a human with Parkinson's Disease or Alzheimer's Disease.

In certain embodiments, the SSRI is selected from the group consisting of bupropion, citalopram, duloxetine, escitalopram, fluoxetine, fluvoxamine, nefazodone, paroxetine, sertraline, sibutramine, trazodone, and venlafaxine.

In one embodiment, the efficacious effect is measured by changes in the Clinical Global Impression Scale (CGI), with emphasis on severity (CGI-S) and improvement (CGI-I) of psychosis. See Busner & Targum, *Psychiatry*, 2007, vol. 4(7): 28-37.

All combinations of the above measurements of efficacy are part of the disclosure provided herein.

In some embodiments, the early or rapid onset of efficacious activity is demonstrated by a greater percentage of patients demonstrating an efficacious effect after a specified period of time as compared to placebo or lack of treatment. In some embodiments, the percentage of patients demonstrating an efficacious effect is increased by greater than about 5%, 10%, 20%, 30%, 40%, 50%, 60%, 70%, 80%, 90%, 100%, 110%, 130%, 150%, 200%, 300%, 400%, or 500%. In some embodiments, the specified period of administration is two weeks, four weeks, six weeks, eight weeks, ten weeks, twelve weeks, fourteen weeks or sixteen weeks before the efficacious effect is demonstrated. In one embodiment, the specified period of time is twelve weeks.

In one embodiment, the Alzheimer's disease psychosis patients are administering one day to four weeks of social interaction therapy, wherein patients who respond sufficiently to the social interaction therapy are excluded from a subsequent clinical study. In one embodiment, three weeks of social interaction therapy is administered.

In one embodiment, the social interaction therapy designed for Alzheimer's disease psychosis patients is a brief psychosocial therapy (BPST). Patients who responded sufficiently to the BPST (i.e., who no longer meet study entry criteria) are excluded from the clinical study. In another embodiment, patients who do not materially improve during this phase are admitted to the treatment period of the clinical study.

In some embodiments, BPST used is as described in Example 1, infra.

Also provided herein is a method for conducting a clinical study in a group of Alzheimer's disease psychosis patients, the method comprising:

(i) screening a group of Alzheimer's disease psychosis patients by administering one day to four weeks of social interaction therapy, wherein patients who respond to the social interaction therapy are excluded from the clinical study;

(ii) dividing the patients who were not excluded into a treatment group and a placebo group;

(iii) administering a drug to the treatment group for a designated period of time; and (iv) evaluating the results of the clinical study by comparing the treatment group to the placebo group.

In another aspect, provided herein are methods for improving hallucinations, delusions, falls, urinary tract infection and/or agitation in a human comprising administering pimavanserin to the human. In some embodiment, pimavanserin is administered in the dose, regimen, etc. as described above. In some embodiments, the human is a possible or probable patient with Alzheimer's Disease.

In another aspect, provided herein are methods for reducing an hallucinations, delusions, falls, urinary tract infection and/or agitation in a human comprising administering pimavanserin to the human. In some embodiment, pimavanserin is administered in the dose, regimen, etc. as described above. In some embodiments, the human is a possible or probable patient with Alzheimer's Disease.

In one embodiment, the efficacious effect is measured by overall reduction of hallucinations, delusions, falls, urinary tract infection and/or agitation. In another embodiment, the efficacious effect is measured by reduced severity of hallucinations, delusions, falls, urinary tract infection and/or agitation. In one embodiment, the efficacious effect is measured by reduced duration of hallucinations, delusions, falls, urinary tract infection and/or agitation. In another embodiment, the efficacious effect is measured by reduced frequency of hallucinations, delusions, falls, urinary tract infection and/or agitation. In one embodiment, the efficacious effect is measured by reduced seriousness of hallucinations, delusions, falls, urinary tract infection and/or agitation. In one embodiment the efficacious effect(s), such as an antipsychotic effect, described herein are in combination with a maintained cognitive status. Thus cognition was not impaired during the 12 week study.

In some embodiments the most reported adverse effect were falls, urinary tract infection and/or agitation.

In some embodiments pimavanserin demonstrated an efficacious effect about 2 times bigger than placebo.

Compound

Pimavanserin, which is also known as N-(1-methylpiperidin-4-yl)-N-(4-fluorophenylmethyl)-N'-(4-(2-methylpropyloxy)phenylmethyl)carbamide, N-[(4-fluorophenyl)methyl]-N-(1-methyl-4-piperidinyl)-N'-[[4-(2-methylpropoxy)phenyl]methyl]-urea, 1-(4-fluorobenzyl)-1-(1-methylpiperidin-4-yl)-3-[4-(2-methylpropoxy)benzyl]urea, or ACP-103. Pimavanserin commonly is administered as pimavanserin tartrate and has the structure of Formula (I):

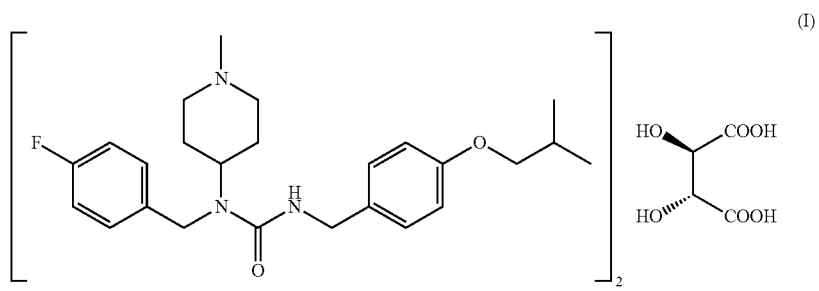

Pimavanserin has previously been synthesized according to the method disclosed in Scheme I.

SCHEME I PREVIOUS SYNTHESIS OF PIMAVANSERIN

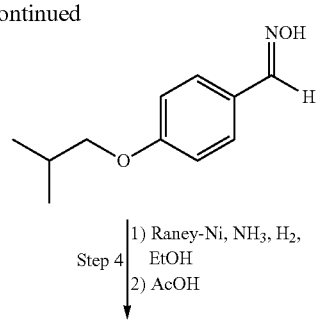

Step 4 1) Raney-Ni, NH₃, H₂, EtOH
2) AcOH

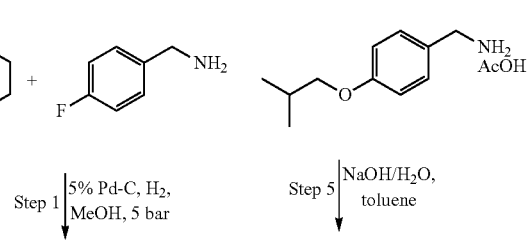

Step 1 5% Pd-C, H₂, MeOH, 5 bar

Step 5 NaOH/H₂O, toluene

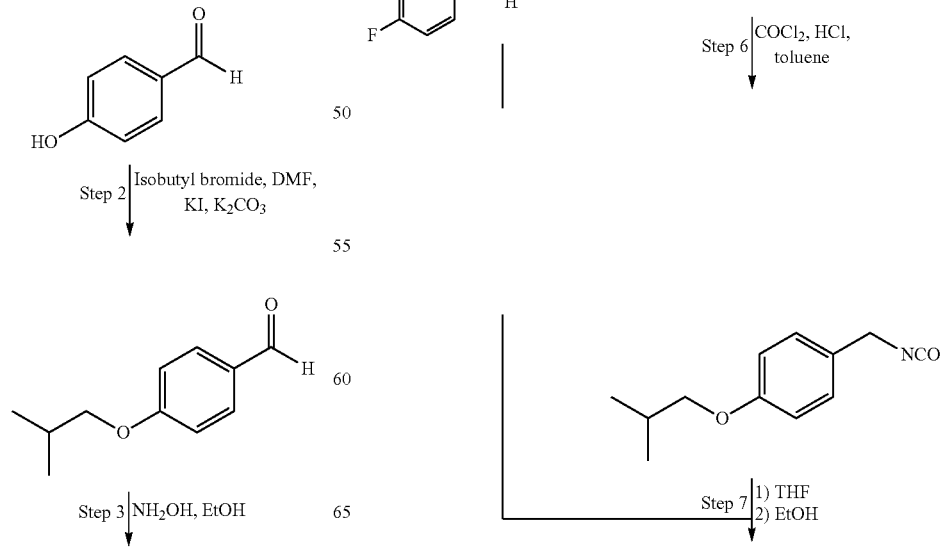

Step 6 COCl₂, HCl, toluene

Step 7 1) THF
2) EtOH

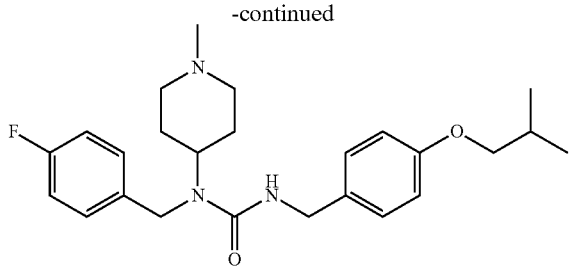

Pimavanserin and methods for its use are described in U.S. Pat. Nos. 7,601,740; 7,659,285; 7,713,995; 7,732,462; 7,994,193 and 8,008,323, the entirety of each of which is hereby incorporated by reference. Pimavanserin can be obtained in a number of salt and crystalline forms. Exemplary pharmaceutically acceptable salts include the tartrate, hemi-tartrate, citrate, fumarate, maleate, malate, phosphate, succinate, sulphate, and edisylate (ethanedisulfonate) salts. Pimavanserin salts including the aforementioned ions, among others, are described in U.S. Patent Publication No. 2006-0111399, filed Sep. 26, 2005, the entirety of which is incorporated herein by reference. In an embodiment provided herein, pimavanserin is the tartrate salt of pimavanserin. Several crystalline forms of the tartrate salt of pimavanserin have been described in U.S. Patent Publication No. 2006-0106063, filed Sep. 26, 2006, the entirety of which is incorporated herein by reference. See also U.S. Pat. Nos. 7,732,615; 7,795,547; 7,790,899; 7,868,176, the entirety of each of which is incorporated herein by reference. In an embodiment provided herein, pimavanserin is the crystalline form of the tartrate salt of pimavanserin Form A. In another embodiment, pimavanserin is the crystalline form of the tartrate salt of pimavanserin Form C. Pimavanserin (including, for example, the tartrate salt) may be formulated into tablets, such as is described in U.S. Patent Publication Nos. 2007-0260064, filed May 15, 2007 and 2007-0264330, filed May 15, 2007, each of which are incorporated herein by reference in their entireties.

Additional methods for manufacturing pimavanserin are described in WO2017/015272, which is incorporated herein by reference in its entireties.

Formulations of pimavanserin are known to those skilled in the art and are commercially available, for example as NUPLAZID® (pimavanserin). NUPLAZID® contains pimavanserin, an atypical antipsychotic, which is present as pimavanserin tartrate salt with the chemical name, urea, N-[(4-fluorophenyl)methyl]-N-(1-methyl-4-piperidinyl)-N'-[[4-(2-methylpropoxy)phenyl]methyl]-,(2R,3R)-2,3-dihydroxybutanedioate (2:1). Pimavanserin tartrate is freely soluble in water. Its molecular formula is $(C_{25}H_{34}FN_3O_2)_2 \cdot C_4H_6O_6$ and its molecular weight is 1005.20 (tartrate salt). The molecular formula of pimavanserin free base is $(C_{25}H_{34}FN_3O_2)_2$ and its molecular weight is 427.55.

NUPLAZID® tablets are intended for oral administration only. Each round, white to off-white, immediate-release, film-coated tablet contains 20 mg of pimavanserin tartrate, which is equivalent to 17 mg of pimavanserin free base. Inactive ingredients include pregelatinized starch, magnesium stearate, and microcrystalline cellulose. Additionally, the following inactive ingredients are present as components of the film coat: hypromellose, talc, titanium dioxide, polyethylene glycol, and saccharin sodium.

In the above formulations, pimavanserin is in crystalline and/or amorphous form.

The pharmacological activity of pimavanserin has been previously reported. See U.S. Patent Publication Nos. 2004/0213816 and 2009/0053329, the entirety of each of which is hereby incorporated by reference. Pimavanserin is active in a number of models thought to be predictive of antipsychotic activity such as DOI ((±)-2,5-dimethoxy-4-iodoamphetamine, a serotonin agonist) induced head twitches in the rat and attenuation of hyperactivity in mice induced by the N-methyl-D-aspartate antagonist MK-801. The compound was effective in these models at oral doses of 3 and 10 mg/kg.

Definitions

Unless defined otherwise, all technical and scientific terms used herein have the same meaning as is commonly understood by one of ordinary skill in the art. In the event that there is a plurality of definitions for a term herein, those in this section prevail unless stated otherwise.

The term "patient" refers to an animal, including, but not limited to, a primate (e.g., human), cow, sheep, goat, horse, dog, cat, rabbit, rat, or mouse. In one embodiment, the patient is a mammalian subject, such as a human. In one embodiment, the subject has or is at risk for a disease, disorder or condition provided herein. In another embodiment, the patient has or is at risk for a disease, disorder or condition wherein the disease, disorder or condition, or a symptom thereof, can be treated, prevented or ameliorated by the administration of pimavanserin. In another embodiment, the patient has a disease, disorder or condition wherein the disease, disorder or condition, or a symptom thereof, can be treated, prevented or ameliorated by the administration of pimavanserin tartrate salt.

The term "pharmaceutically acceptable salt" refers to a salt of a compound that does not cause significant irritation to an organism, such as a human, to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine, lysine, and the like.

The terms "improvement," "improved" and "improves" as used herein with respect to the clinical setting refer to a clinically relevant effect being achieved greater than about 5%, 10%, 20%, 30%, 40%, 50%, 60%, 70%, 80%, 90%, 100%, 110%, 120%, 130%, 140%, 150%, 160%, 170%, 180%, 200%, 300%, 400%, or 500% when compared to baseline after a specified period of time. In some embodiments, the improvement refers to improved efficacious effect in a single patient after the administration of pimavanserin as compared to baseline (i.e., prior to the administration of pimavanserin). In other embodiments, the improvement refers to the demonstration of efficacy by a greater percentage of patients demonstrating an efficacious effect after a specified period of time as compared to placebo or lack of treatment. In various embodiments, the percentage of patients demonstrating an efficacious effect is increased by greater than about 5%, 10%, 20%, 30%, 40%, 50%, 60%, 70%, 80%, 90%, 100%, 110%, 120%, 130%, 140%, 150%, 160%, 170%, 180%, 200%, 300%, 400%, or 500% when compared to placebo or lack of treatment. In some embodiments, the specified period of time is about two weeks, four weeks or six weeks. In one embodiment, the specified period of time is six weeks.

The terms "reduction," "reduced" and "reduces" as used herein with respect to the clinical setting refer to a clinically relevant effect being achieved less than about 5%, 10%, 20%, 30%, 40%, 50%, 60%, 70%, 80%, 90%, 100%, 110%, 120%, 130%, 140%, 150%, 160%, 170%, 180%, 200%, 300%, 400%, or 500% when compared to baseline after a specified period of time or when compared to placebo or lack of treatment. In some embodiments, the specified period of time is about two weeks, four weeks or six weeks. In one embodiment, the specified period of time is six weeks.

As used herein, the term "psychosis subscale" is interchangeable with the term "delusions and hallucinations subscale."

A "baseline score" refers to the score of total NPI-NH score or the score of one domain measured prior to the administration of pimavanserin. In one embodiment, the baseline score is measured on day 0.

EXAMPLES

Example 1: Administration of Pimavanserin to Humans with Ad

A twelve-week, randomized, double-blind, placebo-controlled, single-center study was conducted in ADP patients in nursing homes. A purpose of the study was to evaluate the safety and efficacy of 34 mg pimavanserin compared to placebo in the treatment of ADP.

A total of 181 nursing home patients were enrolled in the study and randomized on a one-to-one basis to receive either 34 mg of pimavanserin or placebo once daily for twelve weeks, following a three-week screening period including brief psycho-social therapy. Patients with Alzheimer's disease (AD) are defined by the National Institute of Neurological and Communicative Disorders and Stroke-Alzheimer's Disease and Related Disorder Association (NINCDS-ADRDA) criteria for possible or probable AD (McKhann et al., Neuro., 1984, vol. 34, 939-944.) The mean age of patients in the study was 86 years.

After completing initial Screening Visit procedures (SV1), patients entered a 3-week screening period with antipsychotic medication washout. During the screening period, the patients received brief psychosocial therapy (BPST; Ballard et al., 2009) following best practice guidelines and safety assessments were performed. After the first Screening Visit (SV1), there were two additional contacts at weekly intervals with the BPST caregiver by phone (SV2 and SV3) to support the patient and the BPST caregiver in this screening phase. Safety assessments were also collected during this phase. At the discretion of the investigator and upon consultation with the Medical Monitor, patients were randomized into the double-blind phase of the study at any time during the screening period if there is a substantial worsening of psychotic symptoms.

Patients were randomized to one of two treatment groups in a 1:1 ratio (pimavanserin 34 mg or placebo), stratified by Baseline Mini-Mental State Examination (MMSE) total score and Neuropsychiatric Inventory-Nursing Home Version (NPI-NH) psychosis score (Domains A and B) (4 levels: MMSE<6 and NPI-NH<12, MMSE>6 and NPI-NH<12, MMSE<6 and NPI-NH>12, MMSE>6 and NPI-NH>12), and entered a 12 week double-blind treatment period.

Nursing home staff administered the study drug to the patient each morning as a single oral dose (2×17 mg tablets) beginning within 24 hours of completion of all baseline assessments (Day 1). During the double-blind treatment period, study visits were performed as follows: Baseline, Day 15, Day 29, Day 43, Day 64, and Day 85 (or early termination). A follow-up telephone safety visit occurred 4 weeks after the last dose of study medication. The NPI-NH psychosis subscale (Delusions+Hallucinations domains) was used to assess psychosis. Behavioral symptoms were assessed using the NPI-NH Total and Individual Behavioral Domain scores and the Cohen-Mansfield Agitation Inventory—Short Form (CMAI-SF). The Alzheimer's disease Cooperative Study-Clinical Global Impression of Change (ADCS-CGIC) was used to assess the patient's overall condition and to address the clinical significance of changes in other psychometric measures. In addition, evaluation of activities of daily living (ADL) was evaluated using the Alzheimer's Disease Cooperative Study-ADL instrument (ADCS-ADL).

Each patient participated in a 3-week screening period, a 12-week double-blind treatment period, and a 4-week follow-up period. The maximum duration of the study for each patient was approximately 19 weeks. Pimavanserin was administered in tablet form, once daily by mouth in 34 mg doses (2 tablets of 17 mg pimavanserin), equivalent to 40 mg pimavanserin tartrate. (2 tablets of 20 mg pimavanserin tartrate) Placebo was administered with visibly matching tablets, using the same route and regimen. The safety of subjects was assessed by monitoring adverse events, physical examinations, vital signs, clinical laboratory tests (hematology, clinical chemistry, and urinalysis), and electrocardiograms. Furthermore cognitive status was assessed via MMSE.

The study included screening period such that patients received up to 3 weeks of brief psychosocial therapy (BPST) designed as per current supportive care guidelines to aid the patient and caregiver in managing the patient's psychotic symptoms through the screening period and minimize placebo response prior to randomization. (Ballard et al., Nat. Rev. Neurol., 2009, vol. May 5(5), 245-255.) BPST followed best practice and consensus guidelines for the treatment of this patient population in which non-pharmacologic therapy is attempted prior to initiation of active pharmacotherapy. Caregivers were trained to perform BPST at the Screening Visit and received a follow-up telephone contact at Screening Visit 2, and at Screening Visit 3. In consultation with the Medical Monitor, randomization prior to completion of the 3 weeks of BPST may occur at the discretion of the Investigator for those patients whose psychotic symptoms substantially worsen during the screening period, and who otherwise meet all eligibility requirements.

BPST was developed for use in clinical trials of Alzheimer's patients with behavioral disorders where placebo response rates often exceed 40%. It has been proposed that these high rates of placebo response result from a combination of Hawthorne effect and spontaneous remission.

Hence, many people may show improvement without active medication and efficacy of pharmacologic treatments may be masked in therapeutic trials. The utility of BPST for the treatment of agitation in Alzheimer's disease (the CALM-AD trial) was recently reported in American Journal of Geriatric Psychiatry (Ballard et al., 2009). In the CALM-AD study, BPST treatment achieved a 6-point reduction on the Cohen-Mansfield Agitation Inventory. In addition, significant reductions in agitation have been reported in two other randomized controlled trials (Cohen-Mansfield et al., 1997 and Cohen-Mansfield et al., 2007).

Patients in the study met the criteria below:
i. Male or female, 50 years of age or older at baseline, with NINCDS-ADRDA defined possible or probable AD.
ii. Have been a nursing home resident for ≥4 weeks prior to randomization, not bedridden and expected to remain in the facility throughout the study.
iii. Have psychotic symptoms that developed after the diagnosis of AD was established. These symptoms must include visual and/or auditory hallucinations, and/or delusions.
iv. Patient must have actively experienced and verbally communicated psychotic symptoms during the month prior to the Screening visit (SV1) and weekly during the previous 2 weeks prior to Baseline.
v. In the opinion of the investigator, the patient requires treatment for their ADP symptoms as evidenced by, for example: distress in the subject, excess disability not attributable to factors other than psychosis, disruptive behavior, interference with medical, nursing or rehabilitative care, and/or dangerous to self or others.
vi. Symptoms must be severe enough at Screening (SV1) and at Baseline to warrant treatment with an antipsychotic agent as documented by Domains A and B of the NPI-NH, and defined as a score of 4 or greater on either the Hallucinations (Frequency×Severity) or Delusions (Frequency×Severity) scales OR a total combined score of 6 or greater.
vii. Patients on acetylcholinesterase inhibitor (AChEI) therapy and/or memantine must be receiving stable doses for 3 months prior to the Baseline visit and during the study.
viii. Female patients must be of non-childbearing potential (defined as either surgically sterilized or at least 1 year postmenopausal) or must agree to use a clinically acceptable method of contraception (such as oral, intrauterine device [IUD; diaphragm], injectable, transdermal or implantable contraception), for at least one month prior to randomization, during the study, and one month following completion of the study.
ix. Willing and able to provide informed consent. If patient is unable to provide written consent due to the severity of dementia, consent must be given by a legally authorized representative.
x. Subject and staff caregiver acting as informant are willing and able to adequately communicate in English for the purposes of the key endpoint assessments by raters.

The antipsychotic efficacy of the administration of pimavanserin to humans with ADP was determined by an improved patient score in the Delusions and Hallucinations subscale of Neuropsychiatric Inventory-Nursing Home Version (NPI-NH) (Delusions+Hallucinations domains A and B) and also by an improved change from Baseline to Day 43 in the Alzheimer's Disease Cooperative Study—Clinical Global Impression of Change (ADCS-CGIC)

The antipsychotic efficacy of the administration of pimavanserin to humans with ADP was determined by an improved patient score in but not limited to (1) the Agitation/Aggression subscale of NPI-NH (Domain C); (2) Sleep/Nighttime Behavior sub scale of NPI-NH (Domain K); (3) Cohen-Mansfield Agitation Inventory—Short Form (CMAI-SF) total score; (4) aggressive behavior subdomain score of CMAI-SF; (5) physically nonaggressive subdomain score of CMAI-SF; and (6) verbally aggressive subdomain score of CMAI-SF.

The antipsychotic efficacy of the administration of pimavanserin to humans with ADP was further determined by an improved patient score in but not limited to (1) NPI-NH total and all remaining individual behavioral domains; (2) Alzheimer's Disease Cooperative Study—Activities of Daily Living Instrument (ADCS-ADL) total score; (3) basic subdomain score of ADCS-ADL; and (4) instrumental subdomain score of ADCS-ADL.

The efficacy of the administration of pimavanserin to humans with agitated behavior and/or aggressive behavior can be determined by an improved patient score in, but not limited to, (1) the Agitation/Aggression subscale of NPI-NH (Domain C), (2) Cohen-Mansfield Agitation Inventory (CMAI or CMAI-SF) total score; (3) aggressive behavior subdomain score of CMAI or CMAI-SF; (4) physically nonaggressive subdomain score of CMAI or CMAI-SF; or (5) verbally aggressive subdomain score of CMAI or CMAI-SF.

The utilization of rescue medications for behavioral disturbance and sleep throughout the administration of pimavanserin was also evaluated to determine the antipsychotic effect. Furthermore, durability of response to pimavanserin in patients with ADP as measured by change from Day 43 to Day 85 of the administration of pimavanserin.

Patients were also evaluated based on cognitive status and cognitive impairment. Pimavanserin demonstrated efficacy on the primary endpoint with a 3.76 point improvement in psychosis at week 6 compared to a 1.93 point improvement for placebo, representing a statistically significant treatment improvement in the NPI-NH Psychosis score (combined hallucinations and delusions domains) (p=0.0451).

Baseline mean scores for the pimavanserin and placebo treated groups were 9.52 and 10.00, respectively.

Pimavanserin demonstrated an efficacy throughout the 12 week study.

Additionally pimavanserin did not impair cognition as measured by the Mini-Mental State Examination (MMSE) score.

Additionally pimavanserin was well tolerated and the safety profile was acceptable.

The results of the study were obtained from a majority of the 181 patients, some of the patients were excluded from the endpoint results but all 181 patients were included in the safety assessment.

Summary of results: pimavanserin demonstrates antipsychotic efficacy as explained below, and hereinabove. In particular, the administration of pimavanserin effectively reduced the NPI-NH psychosis score in patients having a baseline NPI-NH psychosis score of 12 or greater (p=0.0114); the administration of pimavanserin effectively reduced the NPI-NH psychosis score in patients having a baseline of NPI-NH Agitation/Aggression score of 6 or greater (p=0.001); the administration of pimavanserin effectively reduced the NPI-NH psychosis score in patients having a baseline NPI-NH psychosis score of 12 or greater and having a baseline NPI-NH Agitation/Aggression score of 6 or greater (p=0.0010). The administration of pimavanserin also effectively reduced the NPI-NH psychosis score in patients who had prior anti-psychotic use.

Table 2 summarizes the changes of the NPI-NH psychosis score at day 43 compared to the baseline NPI-NH psychosis score for patients in both the pimavanserin group and the placebo group. The delta values (Table 2, column 4) are the differences between the placebo group and pimavanserin group in changes of the patients' NPI-NH psychosis score from the baseline score (at day 0) to day 43 for patients in different subgroups identified respectively. The negative numbers of NPI-NH psychosis scores represent lower NPI-NH psychosis score on day 43 than the baseline score (day 0). Thus, the negative number of NPI-NH psychosis scores represent improvement in the NPI-NH psychosis score.

The pimavanserin arm of the study demonstrated a 4.43 point improvement in psychosis at day 43 for patients having a baseline NPI-NH Psychosis score of 12 or greater (p-value=0.0114; Table 2, row 3), compared to the improvement of 0.42 in patients having a baseline NPI-NH psychosis score of less than 12 (p-value=NS; Table 2, row 2). The results represent a significant (p<0.05) difference of 4.43 points on the Psychosis subscale (sum of scores of Domains A and B) of the NPI-NH. The mean NPI-NH Psychosis score for the pimavanserin arm of patients having a baseline NPI-NH Psychosis score of 12 or greater was reduced by 66.3% from the baseline score of 15.30 to 5.15 at day 43.

The pimavanserin arm of the study also demonstrated a 4.41 point improvement in psychosis at day 43 for patients having a baseline NPI-NH Agitation/Aggression score of 6 or greater (p-value=0.0010; Table 2, row 4), compared to the aggravating of 0.42 in patients having a baseline NPI-NH Agitation/Aggression score of less than 6 (p-value=NS; Table 2, row 5). The results represent a significant (p<0.05) treatment difference of 4.41 points on the Agitation/Aggression subscale (Domains C) of the NPI-NH.

In addition, the pimavanserin arm of the study also demonstrated a 1.13 points improvement on the Agitation/Aggression subscale (Domain C) of the NPI-NH (vs. an improvement of 0.47 in the placebo arm).

Moreover, the pimavanserin arm demonstrated an improvement of 7.18 in psychosis at day 43 for patients having a baseline NPI-NH Psychosis score of 12 or greater as well as a baseline Agitation/Aggression score of 6 or greater (p-value=0.0010; Table 2, row 6).

Furthermore, the pimavanserin arm of the study also demonstrated a 6.53 point improvement in psychosis at day 43 for patients that had anti-psychotic use prior to the baseline measurement on day 0 (p-value=NS; Table 2, row 7), compared the improvement in patients that had no anti-psychotic use prior to the baseline measurement on day 0 (p-value=0.0374; Table 2, row 8). The results represent an improvement of 6.53 points on the Agitation/Aggression subscale (Domains C) of the NPI-NH.

In addition, subgroup analysis showed that patients with a concomitant Selective Serotonin Reuptake Inhibitor (SSRI) use had a treatment effect larger than those with no concomitant SSRI use.

Pimavanserin was safe and well tolerated in this study. The most common adverse events were falls (23.1% in placebo arm vs. 23.3% in pimavanserin arm) and urinary tract infection (27.5% in placebo arm vs. 22.2% in pimavanserin arm). The study results showed no negative effect on cognitive function or motor functions in both placebo arm and pimavanserin arm.

TABLE 2

Change of NPI-NH Psychosis Score in Patients on Day 43.

| NPI-NH PSYCHOSIS SCORE at day 43 | Placebo Group | Pimavanserin Group | Delta | Effect Size | P-Value |
| --- | --- | --- | --- | --- | --- |
| Baseline NPI-NH Psychosis Score <12 (n = 57) | −0.16 | −0.58 | −0.42 | −0.077 | NS |
| Baseline NPI-NH Psychosis score ≥12 (n = 121) | −5.72 | −10.15 | −4.43 | −0.734 | 0.0114 |
| Baseline Agitation/Aggression Score <6* (n = 85) | −2.08 | −1.40 | 0.68 | 0.122 | NS |
| Baseline Agitation/Aggression Score ≥6* (n = 93) | −1.68 | −6.09 | −4.41 | −0.778 | 0.0010 |
| Baseline NPI-NH Psychosis Score ≥12 & Agitation/Aggression Score ≥6* (n = 38) | −3.75 | −10.93 | −7.18 | −1.225 | 0.0010 |
| Prior Anti-psychotic use (n = 16) | 5.01 | −1.52 | −6.53 | −0.905 | NS |
| No Prior Anti-psychotic use (n = 162) | −2.24 | −4.15 | −1.90 | −0.351 | 0.0374 |

*post-hoc analysis
NS = not significant; n = number of patients in the identified subgroup.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method for the treatment of delusions and/or hallucinations in a human with dementia, comprising orally administering 34 mg of pimavanserin to the human, wherein the human:
   has a baseline score of 12 or greater in the Psychosis subscale (Domains A and B) of the NPI-NH; or
   has a baseline score of 6 or greater in the Agitation/Aggression subscale (Domain C) of the NPI-NH;
   wherein the effect of the treatment is determined by an improved patient score in the NPI-NH of at least 4 points as compared to baseline score prior to administering pimavanserin.

2. The method of claim 1, wherein the human has a baseline score of 12 or greater in the Psychosis subscale (Domains A and B) of the NPI-NH.

3. The method of claim 1, wherein the human has a baseline score of 6 or greater in the Agitation/Aggression subscale (Domain C) of the NPI-NH.

4. The method of claim 1, wherein the human has a baseline score of 12 or greater in the Psychosis subscale (Domains A and B) of the NPI-NH and has a baseline score of 6 or greater in the Agitation/Aggression subscale (Domain C) of the NPI-NH.

5. The method of claim 1, wherein the Psychosis subscale of the NPI-NH is a combination of Delusions (Domain A) and Hallucinations (Domain B) of the NPI-NH.

6. The method of claim 1, wherein the effect is determined by an improved patient score at least about 6 weeks from the initial administration of pimavanserin.

7. The method of claim 1, wherein the p-value of the improvement is between 0.0001 and 0.05.

8. The method of claim 1, wherein a tartrate salt of pimavanserin is administered to the human.

9. The method of claim 1, wherein pimavanserin is administered during concomitant administration of an anti-Alzheimer's agent.

10. The method of claim 9, wherein the anti-Alzheimer's agent is an acetylcholinesterase inhibitor.

11. The method of claim 9, wherein the anti-Alzheimer's agent is selected from the group consisting of memantine, rivastigmine, tacrine, donepezil, verubecestat and galantamine.

12. The method of claim 1, wherein the cognitive status of the human is not impaired.

13. The method of claim 12, wherein the cognitive status is determined by the Mini-Mental State Examiner (MMSE) score.

14. The method of claim 1, further comprising:
Determining an baseline score on the NPI-NH for a human; and
Identifying a human with a score of 12 or greater in the Psychosis subscale (Domains A and B) of the NPI-NH prior to administering pimavanserin to the human.

15. The method of claim 1, further comprising:
Determining an baseline score on the NPI-NH for a human; and
Identifying a human with a score of 6 or greater in the Agitation/Aggression subscale (Domain C) of the NPI-NH prior to administering pimavanserin to the human.

16. The methods of claim 1, wherein the human is a human diagnosed with Parkinson's Disease or Alzheimer's Disease.

* * * * *